United States Patent
Schaus et al.

(10) Patent No.: US 6,864,262 B2
(45) Date of Patent: Mar. 8, 2005

(54) 1-(2-M-METHANESULFONAMIDOPHENYLETHYL)-4-(M-TRIFLUOROMETHYLPHENYL) PIPERAZINE AND PHARMACEUTICALLY ACCEPTABLE SALTS AND SOLVENTS THEREOF

(75) Inventors: John Mehnert Schaus, Zionsville, IN (US); Dennis Charles Thompson, Indianapolis, IN (US); Karl Bruce Thor, Morrisville, NC (US)

(73) Assignee: Eli Lilly and Company, Indianapolis, IN (US)

( * ) Notice: Subject to any disclaimer, the term of this patent is extended or adjusted under 35 U.S.C. 154(b) by 82 days.

(21) Appl. No.: 10/432,413

(22) PCT Filed: Nov. 16, 2001

(86) PCT No.: PCT/US01/42949

§ 371 (c)(1),
(2), (4) Date: May 21, 2003

(87) PCT Pub. No.: WO02/44159

PCT Pub. Date: Jun. 6, 2002

(65) Prior Publication Data

US 2004/0067962 A1 Apr. 8, 2004

Related U.S. Application Data

(60) Provisional application No. 60/250,203, filed on Nov. 29, 2000.

(51) Int. Cl.[7] .................. A61K 31/495; C07D 295/135
(52) U.S. Cl. ................................. 514/255.03; 544/392
(58) Field of Search ...................... 544/392; 514/255.03

(56) References Cited

U.S. PATENT DOCUMENTS

| | | |
|---|---|---|
| 3,170,926 A | 2/1965 | Ash et al. |
| 3,717,634 A | 2/1973 | Wu et al. |
| 3,957,786 A | 5/1976 | Klemm et al. |
| 4,196,209 A | 4/1980 | Dumont et al. |
| 4,423,049 A | 12/1983 | Temple, Jr. et al. |
| 4,818,756 A | 4/1989 | Seidel et al. |
| 4,833,142 A | 5/1989 | Hartog et al. |
| 4,997,841 A | 3/1991 | Oxford et al. |
| 5,298,520 A | 3/1994 | Baker et al. |
| 5,340,810 A | 8/1994 | Clitherow et al. |
| 5,434,154 A | 7/1995 | Smith et al. |
| 5,466,699 A | 11/1995 | Robertson et al. |
| 5,521,188 A | 5/1996 | Gylys et al. |
| 5,545,644 A | 8/1996 | Macor et al. |
| 5,624,952 A | 4/1997 | Van Lommen et al. |
| 5,801,170 A | 9/1998 | Gaster et al. |

FOREIGN PATENT DOCUMENTS

| | | |
|---|---|---|
| EP | 0 955 741 A1 | 4/2000 |
| WO | WO 90/06927 | 6/1990 |
| WO | WO 97/23466 A | 7/1997 |

OTHER PUBLICATIONS

Besson, et al., *Pain Headache*, 9, 64–100 (1987).
Hosoya, et al., *Exp. Brain Res.*, 86, 224–228, (1991).
M. Kojima, et al., *Cell Tissue Res.*, 30 229..23–36 (1983).
N. Rajaofetra, J. *Comzp. Neurol.*, 318. 1–17 (1992).
K.B. Thor, et al., *Neuroscience*, 55, 235–252 (1993).
M.J. Epsey, et al., *Eur., J.. Phannacol.*, 221L 167–170 (1992).
Fakuda, et al., *Exp. Brain Res.*, 83,303–316 (1991).
McMahon, et al., *Brain Res.*, 234., 237–249 (1982).
Steers, et al., *Am. J. Physiol.*, R1441–1449 (1989).
K.B. Thor, et al., *Brain Res. Dev. Brain Res.*, 54, 35–42 (1990).
Thor, et al., *Phanylacol. Expt. 5 77*Ter., 1014–1024 (1996);, 1998).
Hamon, et al., *Neuropsychophaninacol.*, 3(5/6), 349–360 10 (1990).
Leonhardt, et al., *J. Neurochemn.*, 53 (2), 465–471 (1989).
Adham et al. (*Proc. Natl. Acad. Sci. USA*, 90, 408–412 (1993)).
Barf et al. J. Med. Chem. (1996), 39(24) 4717–4726.

*Primary Examiner*—Emily Bernhardt
(74) *Attorney, Agent, or Firm*—R. Craig Tucker

(57) ABSTRACT

The present invention provides a compound of the formula (I)

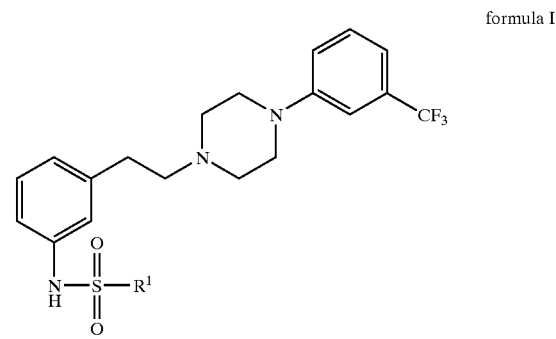

formula I and the pharmaceutically acceptable salts and solvates thereof, which is useful for treating bladder overactivity or urinary incontinence.

10 Claims, 21 Drawing Sheets

Control Acetic Acid

External Urethral Sphincter

Bladder Pressure

50 μV
40 cm H2O
1 min

↑ R

A. LY217101

A. LY217101

B. LY217101 post WAY100635 (0.3 mg/kg)

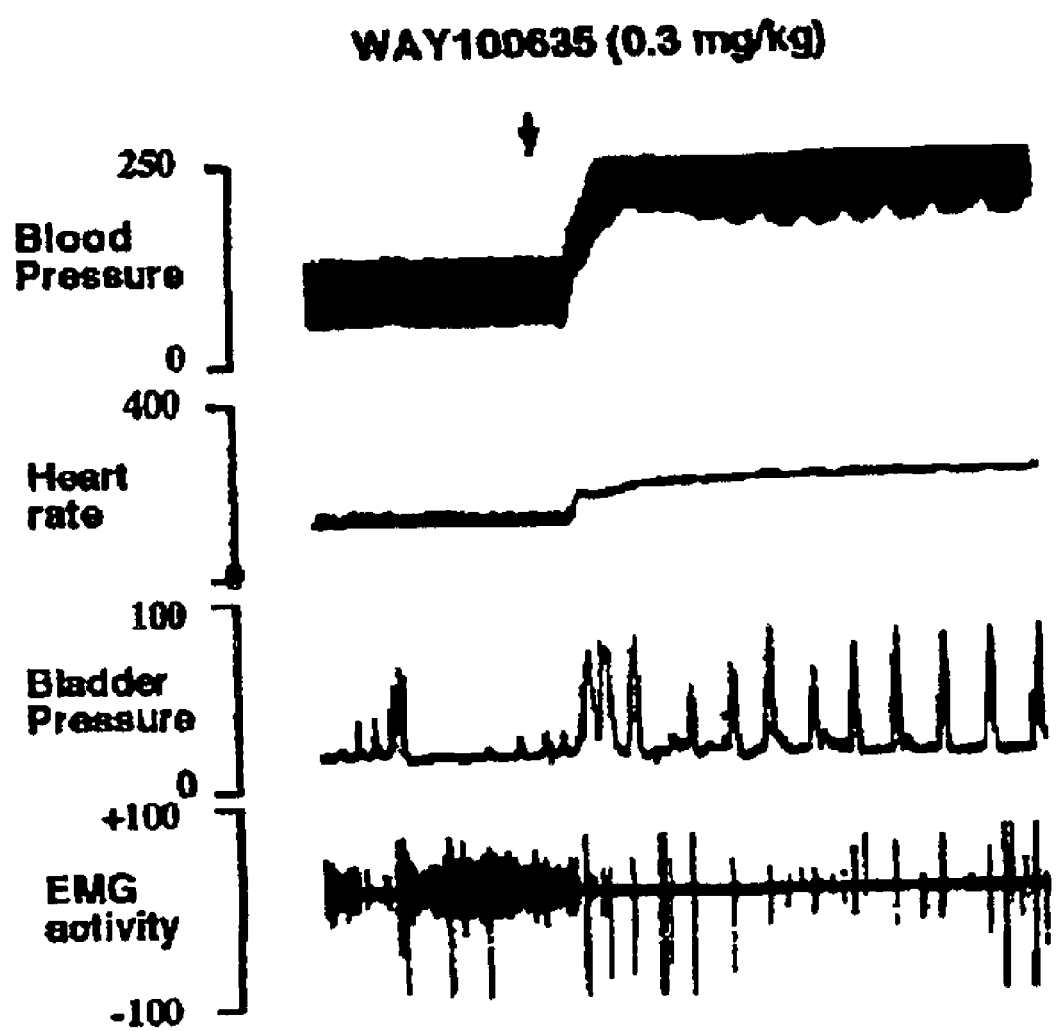

US 6,864,262 B2

1-(2-M-METHANESULFONAMIDOPHENYLETHYL)-4-(M-TRIFLUOROMETHYLPHENYL) PIPERAZINE AND PHARMACEUTICALLY ACCEPTABLE SALTS AND SOLVENTS THEREOF

This U.S. national stage application of International Application PCT/US01/42949, filed Nov. 16, 2001, claims priority to U.S. provisional application Ser. No. 60/250,203, filed Nov. 29, 2000.

BACKGROUND OF THE INVENTION

Bladder over-activity and urinary incontinence are common conditions that present various symptoms that are at best embarrassing and at worst disabling. These conditions are a frequent cause of elderly people's confinement to nursing homes and other protected environments. While they are more common among women than among men, at all ages, these conditions afflict significant numbers of both sexes. It is well known that many children past the usual age of toilet-training suffer from nocturnal enuresis, and that the elderly are quite likely to develop bladder over-activity or urinary incontinence as they grow older. However, some studies have reported daily incontinence among as many as 17% of young, apparently healthy, women. Thus, it is clear that reliable and safe methods of treating bladder over-activity and urinary incontinence are seriously needed.

Bladder over-activity and urinary incontinence can result from various neurological disorders; such as Parkinson's Disease, multiple sclerosis, spinal cord injury, stroke, and Alzheimer's Disease. Bladder over-activity can also result from various disorders localized to the lower urinary tract; such as prostatitis, prostatodynia, urethritis, interstitial cystitis, urinary tract infection, outlet obstruction, benign prostate hyperplasia, radiation therapy of the pelvic viscera, diabetes, or vulvodynia. Bladder over-activity can also be idiopathic.

Thus, it is clear that bladder over-activity and urinary incontinence are major disorders of today. It is believed to afflict approximately 12 million people in the United States alone, and to occur in from 15 to 30% of the population over the age of 60. Its treatment at present is quite unsatisfactory.

The therapies currently used for certain conditions listed above often do not resolve bladder over-activity and incontinence. For example, L-dopa treats the motor symptoms of Parkinson's disease, but can actually exacerbate bladder over-activity. Likewise, surgical removal of the prostate and the use of alpha adrenergic receptor antagonists can improve urine flow and decrease residual urine, but the symptoms of frequency, urgency, and nocturia often persist.

The mainstay therapy for treatment of bladder over-activity and incontinence are drugs that are muscarinic cholinergic receptor antagonists ("anticholinergics") with varying degrees of calcium channel blocking activity. The only compounds prescribed in significant quantities are tolterodine and oxybutynin. Off-label use of tricyclic antidepressants, such as imipramine, which also exhibit significant anticholinergic properties is also practiced. These compounds work by blocking the excitatory effects of acetylcholine on the bladder smooth muscle, thus suppressing bladder contractions and reducing bladder over-activity. Unfortunately, these compounds not only suppress bladder over-activity, but they also suppress normal bladder activity, which results in increases in residual urine, i.e., the bladder does not empty completely and the remaining urine provides a medium for bacterial growth and subsequent urinary tract infections. A potential increase in residual volume is especially problematic for BPH patients who already have problems with residual urine due to obstruction of the urine outlet, i.e., the urethra. Thus, anticholinergic drugs are contraindicated for BPH patients. In addition, all of these "anticholinergics" cause undesirable side-effects typical of anticholinergic drugs such as dry mouth, constipation, etc., and the efficacy of anticholinergic compounds is only partial.

Currently, there are no medicines indicated for the treatment of stress urinary incontinence. Off-label use of sympathomimetics, such as psuedoephidrine, is practiced, but the efficacy is questionable. The only therapies currently recognized by physicians are behavioral modification, pelvic floor exercises, and surgery.

Over the last several years, various studies have implicated the neurotransmitter serotonin (5-hydroxytryptamine, 5HT) in control of lower urinary tract function. 5HT terminals and various receptor subtypes are intimately associated with spinal cord areas that contain afferent and efferent components of lower urinary tract neural control centers (Besson and Chaouch, *Pain Headache*, 9, 64–100 (1987); Y. Hosoya, et al., *Exp. Brain Res.*, 86, 224–228, (1991); M. Kojima, et al., *Cell Tissue Res.*, 229, 23–36 (1983); N. Rajaofetra, *J. Comp. Neurol.*, 318, 1–17 (1992); K. B. Thor, et al., *Neuroscience*, 55, 235–252 (1993)). Pharmacological and physiological studies have indicated that the prevailing effects of 5HT receptor activation on the urinary bladder are inhibitory. (M. J. Epsey, et al., *Eur., J. Pharmacol.*, 221, 167–170 (1992); Fakuda and Koga, *Exp. Brain Res.*, 83,303–316 (1991); McMahon and Spillane, *Brain Res.*, 234, 237–249 (1982); Steers and deGroat, *Am. J. Physiol.*, R1441–1449 (1989); K. B. Thor, et al., *Brain Res. Dev. Brain Res.*, 54, 35–42 (1990); Thor and Katofiasc, *J. Pharmacol. Expt. Ther.*, 274, 1014–1024 (1996); and Thor et al., 1998).

It has been recognized that there are multiple types of 5-HT receptors. These receptors have been classified as 5-HT$_1$, 5-HT$_2$, 5-HT$_3$, 5-HT$_4$, 5-HT$_5$, 5HT$_6$ and 5-HT$_7$. The most heterogeneous of these classes appears to be 5-HT$_1$, subclassified as: 5-HT$_{1A}$, 5-HT$_{1B}$, and 5-HT$_{1D}$ (Hamon et al., *Neuropsychopharmacol.*, 3(5/6), 349–360 (1990)) and 5-HT$_{1E}$ (Leonhardt et al., *J. Neurochem.*, 53 (2), 465–471 (1989)). A human gene which expresses an additional 5-HT$_1$ subclass, 5-HT$_{1F}$ was isolated by Kao and coworkers (*Proc. Natl. Acad. Sci. USA*, 90, 408–412 (1993)).

Thus, it is clear that there is an unmet medical need for pharmaceuticals that are effective for the treatment of bladder over-activity and urinary incontinence, and free from undesired side effects. The present invention provides such pharmaceuticals.

BRIEF DESCRIPTION OF THE DRAWINGS

FIGS. 7A, 7B, and 7C—The effect of the administration, in a single experiment, of LY217101, followed first by the administration of WAY100635, and secondly by the administration of LY217101, on bladder capacity, heart rate, bladder pressure, and external urethral sphincter EMG activity.

SUMMARY OF THE INVENTION

Figure 1A:
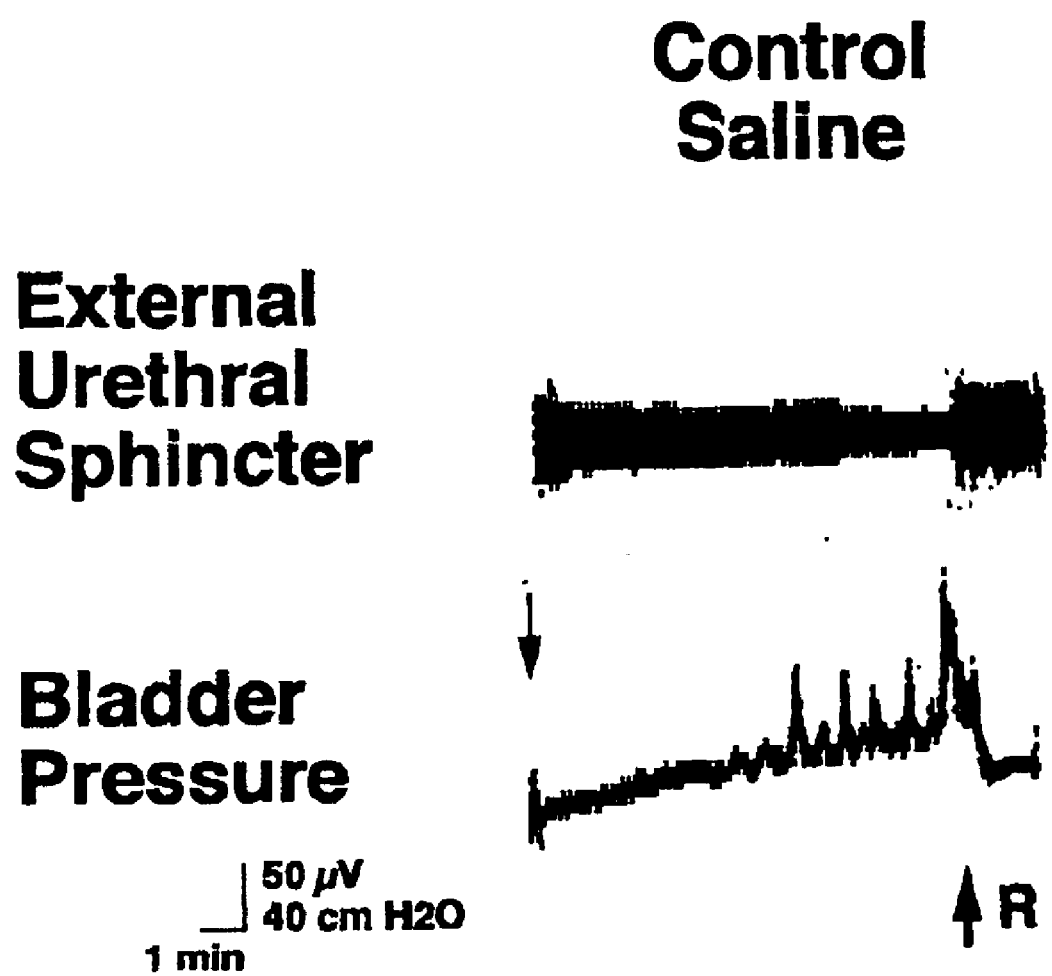
FIGS. 1A, 1B, and 1C—The effect of control infusion of saline, control infusion of acetic acid and after GR127935 during the infusion of acetic acid on the activity of external urethral sphincter EMG and bladder pressure.

The present invention provides compounds of formula I:

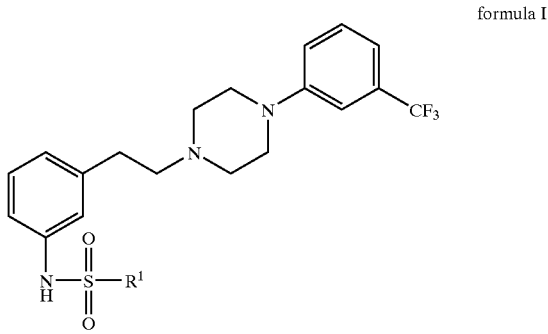

formula I wherein $R^1$ represents $C_1$–$C_4$ alkyl;
and the pharmaceutically acceptable salts and solvates thereof.

In accordance with the present invention, there is provided a method of treating bladder over-activity or urinary incontinence in a patient in need of such treatment, comprising administering to the patient an effective amount of a combined 5-$HT_{1B}$ and 5-$HT_{1D}$ receptor agonist.

The present invention also provides a method of treating bladder over-activity or urinary incontinence in a patient in need of such treatment, comprising administering to the patient an effective amount of a combined 5-$HT_{1A}$, 5-$HT_{1B}$ and 5-$HT_{1D}$ receptor agonist.

The present invention further provides a method of treating bladder over-activity or urinary incontinence in a patient in need of such treatment, comprising administering to the patient an effective amount of a 5-$HT_{1B}$ receptor agonist in combination with a 5-$HT_{1D}$ receptor agonist.

Additionally, the present invention provides a method of treating bladder over-activity or urinary incontinence in a patient in need of such treatment, comprising administering to the patient an effective amount of a 5-$HT_{1A}$ receptor agonist in combination with a 5-$HT_{1B}$ receptor agonist and 5-$HT_{1D}$ receptor agonist.

Furthermore, the present invention provides a method of treating bladder over-activity or urinary incontinence in a patient in need of such treatment, comprising administering to the patient an effective amount of a compound of formula I.

According to another aspect, the present invention provides the use of a compound of formula I, or a pharmaceutically acceptable salt thereof for the manufacture of a medicament for treating bladder over-activity or urinary incontinence.

In addition, the present invention provides the use of a compound of formula I, or a pharmaceutically acceptable salt thereof for treating bladder over-activity or urinary incontinence.

Furthermore, the present invention provides a pharmaceutical composition comprising an effective amount of a compound of formula I and one or more pharmaceutically acceptable diluents or carriers.

The invention further provides a process for preparing a compound of formula I

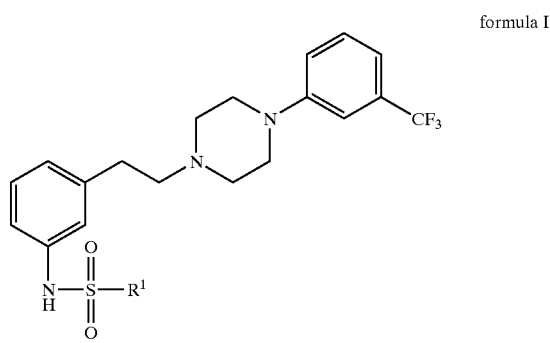

formula I wherein $R^1$ represents $C_1$–$C_4$ alkyl, comprising sulfonylating a compound of the formula;

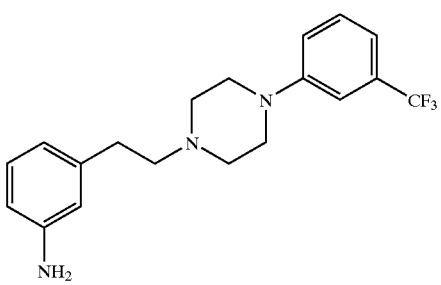

with a compound of the formula;
$C_1$–$C_4$alkylSO$_2$Lg;
wherein Lg is a suitable leaving group.

Furthermore, the invention provides a compound of the formula;

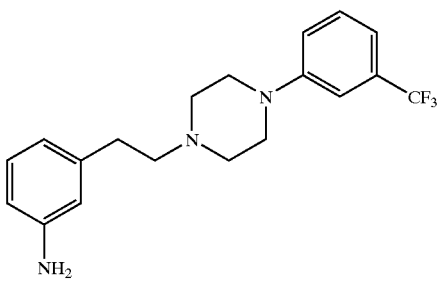

DETAILED DESCRIPTION OF THE INVENTION

As used herein the term "LY217101" refers to 1-(2-m-methanesulfonamidophenylethyl)-4-(m-trifluoromethylphenyl)piperazine (see example 1 below).

As used herein the term "$C_1$–$C_4$ alkyl" refers to straight or branched, monovalent, saturated aliphatic chains of 1 to 4 carbon atoms and includes, but is not limited to, methyl, ethyl, propyl, isopropyl, butyl, isobutyl, and t-butyl. It is understood that with regard to substituent $R^1$, methyl is preferred.

The present invention includes the hydrates and the pharmaceutically acceptable salts and solvates of the compound defined by formula I. The compound of this invention can possess a sufficiently basic functional group, and accordingly react with any of a number of inorganic and organic acids, to form a pharmaceutically acceptable salt.

The term "pharmaceutically acceptable salt" as used herein, refers to salts of the compound of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science*, 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymaleate, mandelate, mesylate, nicotinate, isonicotinate, cinnamate, hippurate, nitrate, stearate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, hemi-tartrate, benzenesulfonate, methanesulfonate, ethanesulfonate, propanesulfonate, hydroxyethanesulfonate, 1-naphthalenesulfonate, 2-napththalenesulfonate, 1,5-naphthalenedisulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid. Preferred pharmaceutically acceptable salts are hydrochloride, hydrobromide, oxalate, maleate, methanesulfonate, and hemi-tartrate. The most preferred pharmaceutically acceptable salt is hydrochloride.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, methanolates, ethanolates, acetonitrilates and the like.

The compound of formula I can be prepared by techniques and procedures readily available to one of ordinary skill in the art, for example by following the procedures as set forth in Scheme I. All substituents, unless otherwise indicated, are previously defined. The reagents and starting materials are readily available to one of ordinary skill in the art.

Scheme I

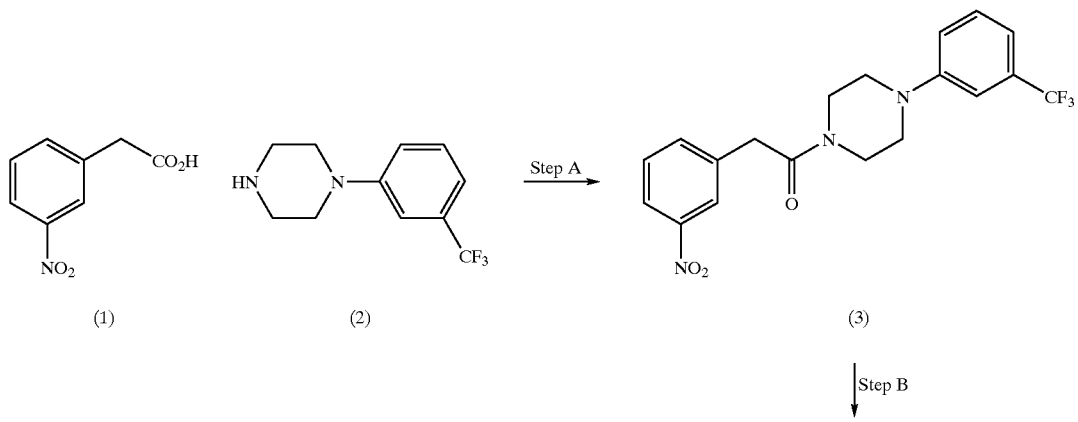

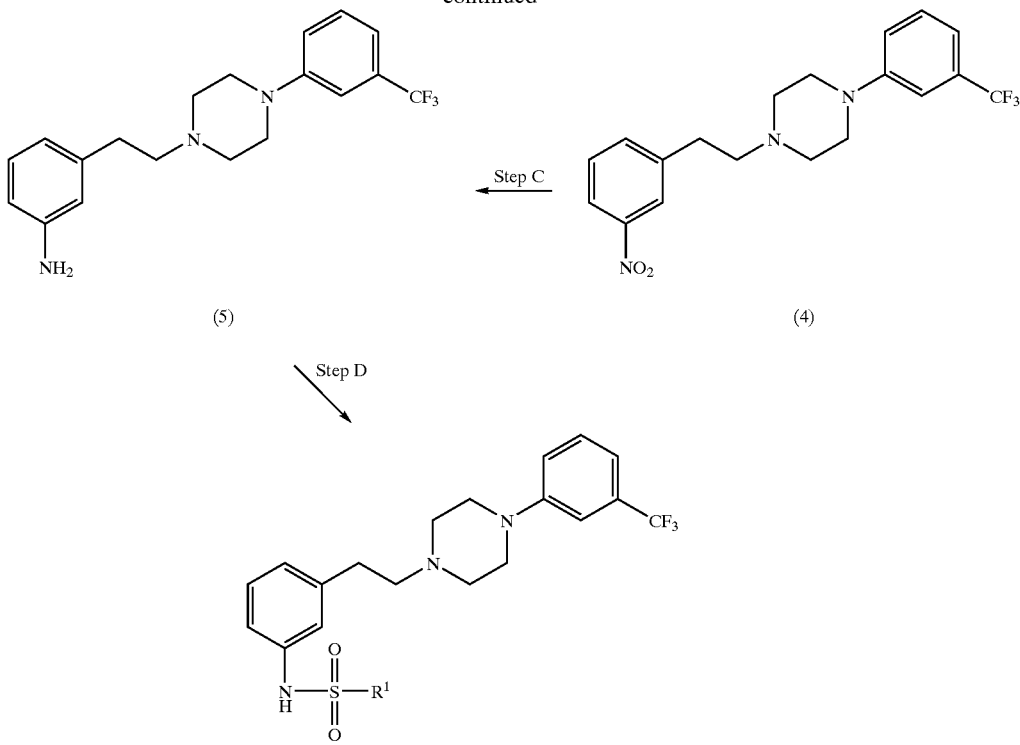

formula I

In Scheme I, step A, 3-nitrophenylacetic acid (1) is coupled with N-(α,α,α-trifluoro-m-tolyl)piperazine (2) under conditions well known in the art to provide the amide (3). For example, 3-nitrophenylacetic acid (1) is dissolved in a suitable organic solvent, such as toluene and treated with an excess of oxalyl chloride. The reaction is allowed to stir at room temperature for about 1 to 3 hours and then carefully heated until an exotherm occurs. After the exotherm subsides, the reaction is heated at reflux for about 2 to 4 hours and then concentrated to provide the acid chloride. The acid chloride is then dissolved in a suitable organic solvent, such as acetone, and the solution is added dropwise to a stirring solution of one equivalent of N-(α,α,α-trifluoro-m-tolyl)piperazine (2), and one equivalent of a suitable base, such as sodium carbonate, in a suitable solvent mixture, such as water/acetone (1:1). The temperature is maintained below 30° C. After addition is complete, the reaction is stirred for about 16 hours at room temperature. The amide (3) is then isolated by techniques well known in the art, such as extraction. For example, the acetone is essentially evaporated and the remaining aqueous is extracted with a suitable organic solvent, such as diethyl ether. The organic extracts are combined, washed with water, 2N HCl, brine, dried over anhydrous sodium sulfate, filtered and concentrated under vacuum to provide the amide (3).

In Scheme I, step B, amide (3) is reduced under standard conditions to provide the piperazine (4). For example, amide (3) is dissolved in a suitable organic solvent, such as tetrahydrofuran and then added to a suitable reducing agent, such as borane. The reaction is stirred at room temperature for about 10 to 20 hours. It is then cooled to about 0° C. to 5° C. and treated with aqueous acid, such as 2N HCl. The organic solvent is then evaporated from the reaction mixture and excess aqueous acid is added, such as 6N HCl. The mixture is then heated at about 90° C. for about 1 hour. The piperazine (4) is then isolated and purified by techniques well known in the art, such as extraction. For example, the cooled mixture is treated with a suitable aqueous base, such as sodium hydroxide solution to achieve a pH of greater than 12. The basified solution is then extracted with a suitable organic solvent, such as diethyl ether. The organic extracts are combined, washed with water, brine, dried over anhydrous sodium sulfate, filtered and concentrated under vacuum to provide piperazine (4).

In Scheme I, step C, piperazine (4) is further reduced under conditions well known in the art to provide the amine (5). For example, the piperazine (4) is dissolved in a suitable organic solvent, such as ethanol, and the solution is treated with a catalytic amount of Raney nickel. The reaction mixture is then placed under hydrogen at about 60 psi. The reaction is hydrogenated at room temperature for about 2 hours. The product is then isolated and purified using known techniques and procedures. For example, the reaction mixture is filtered and the filtrate is concentrated under vacuum. The crude residue is then recrystallized from a suitable organic solvent, such as hexanes to provide the purified amine (5).

In Scheme I, step D, amine (5) is sulfonylated under standard conditions with a compound of formula $C_1$–$C_4$alkylSO$_2$Lg to provide the $C_1$–$C_4$alkylsulfonamide of formula I under conditions well known in the art. Lg represents a suitable leaving group, such as Cl, Br, and the like. For example, amine (5) is dissolved in a suitable organic solvent, such as pyridine and cooled to less than 10° C. The solution is then treated with about 1.25 equivalents of $C_1$–$C_4$alkylSO$_2$Lg, such as methanesulfonyl chloride. The reaction is then stirred at room temperature for about 10 to 20 hours. The $C_1$–$C_4$alkylsulfonamide of formula I is then isolated and purified under using standard techniques, such as extraction and chromatography. For example, the above reaction mixture is poured into cold water and the mixture is extracted with a suitable organic solvent, such as diethyl ether. The organic extracts are combined, washed with water, brine, dried over anhydrous sodium sulfate, filtered and concentrated under vacuum. The crude residue is then purified by flash chromatography on silica gel with a suitable eluent, such as methylene chloride/methanol to provide the purified $C_1$–$C_4$alkylsulfonamide of formula I as the free base.

The pharmaceutically acceptable salt of formula I is readily prepared by one of ordinary skill in the art. For example, the free base is dissolved in a suitable organic solvent, such as methanol or a mixture of methanol/diethyl ether, and treated with an acid, such as oxalic acid or hydrochloric acid. The solvent is evaporated and the residue is recrystallized from a suitable solvent such as ethyl acetate/methanol to provide the pharmaceutically acceptable salt of the compound of formula I.

Table I depicts the results of the binding affinity as a $K_i$ in nM or % displacement of 1-(2-m-methanesulfonamidophenylethyl)-4-(m-trifluoromethylphenyl)piperazine as compared to 1-(2-p-methanesulfonamidophenylethyl)-4-(m-trifluoromethylphenyl)piperazine (see U.S. Pat. No. 3,170,926) at six serotonin receptors.

The present invention provides a method of treating bladder over-activity or urinary incontinence in a patient in need of such treatment, comprising administering to the patient an effective amount of a combined 5-$HT_{1B}$ and 5-$HT_{1D}$ receptor agonist.

The term "combined 5-$HT_{1B}$ and 5-$HT_{1D}$ receptor agonist", as it is used in the description of the present invention, is taken to mean a compound which is a full or partial agonist at the 5-$HT_{1B}$ and 5-$HT_{1D}$ receptors. A compound which is a partial agonist at the 5-$HT_{1B}$ and 5-$HT_{1D}$ receptor must exhibit sufficient activity to increase bladder capacity and sphincter EMG activity by at least 20%. While a partial agonist of any intrinsic activity may be useful for the method of this invention, partial agonists of at least about 50% agonist effect ($E_{max}$) are preferred and partial agonists of at least about 80% agonist effect ($E_{max}$) are more preferred. Full agonists at the 5-$HT_{1B}$ and 5-$HT_{1D}$ receptors are most preferred.

Suitable combined 5-$HT_{1B}$ and 5-$HT_{1D}$ receptor agonists include, but are not limited to, RU24969, GR127935, eletriptan, zolmitriptan, naratriptan, rizatriptan, avitriptan, anpirtoline, alniditan, BMS-181885—(3-[3-[4-(5-methoxy-4-pyrimidyl)-1-piperazinyl]propyl]-5-(1,2-dioxo-4-methyl-3-cyclobuten-3-yl)amino-1H-indole), and all dimerizations of the above compounds.

The above-listed compounds are commercially available or are readily prepared by one of ordinary skill in the art

TABLE I

| Receptor | 1-(2-m-methanesulfonamidophenylethyl)-4-(m-trifluoromethylphenyl)piperazine | 1-(2-p-methanesulfonamidophenylethyl)-4-(m-trifluoromethylphenyl)piperazine |
|---|---|---|
| 5-$HT_{1B}$ | 1.7 nM | 9.49 nM |
| 5-$HT_{1D}$ | 1.2 nM | 55.3 nM |
| 5-$HT_{1A}$ | 0.95 nM | 3.45 |
| 5-$HT_{1E}$ | 3876 nM | 5% @ 1000 nM |
| 5-$HT_{1F}$ | 32.3 nM | 14% @ 1000 nM |
| 5-$HT_7$ | 103.8 nM | 45 |

Table I reveals that 1-(2-m-methanesulfonamidophenylethyl)-4-(m-trifluoromethylphenyl)piperazine has a 56-fold higher affinity for the 5-$HT_{1B}$ receptor than 1-(2-p-methanesulfonamidophenylethyl)-4-(m-trifluoromethylphenyl)piperazine. In addition, Table I reveals that 1-(2-m-methanesulfonamidophenylethyl)-4-(m-trifluoromethylphenyl)piperazine has a 45-fold higher affinity for the 5-$HT_{1D}$ receptor than 1-(2-p-methanesulfonamidophenylethyl)-4-(m-trifluoromethylphenyl)piperazine. The above data supports the conclusion that 1-(2-m-methanesulfonamidophenylethyl)-4-(m-trifluoromethylphenyl)piperazine has surprising and unexpectedly high binding affinity for the 5-$HT_{1B}$ and 5-$HT_{1D}$ receptors as compared to the corresponding regioisomer, 1-(2-p-methanesulfonamidophenylethyl)-4-(m-trifluoromethylphenyl)piperazine.

following known processes and procedures, for example, see U.S. Pat. Nos. 4,196,209, 5,340,810, 5,545,644, 5,466,699, 4,997,841, 5,298,520, 5,434,154, 5,624,952, and 5,521,188.

In addition, the present invention provides a method of treating bladder over-activity or urinary incontinence in a patient in need of such treatment, comprising administering to the patient an effective amount of a combined 5-$HT_{1A}$, 5-$HT_{1B}$ and 5-$HT_{1D}$ receptor agonist.

The term "combined 5-$HT_{1A}$, 5-$HT_{1B}$ and 5-$HT_{1D}$ receptor agonist", as it is used in the description of the present invention, is taken to mean a compound which is a full or partial agonist at the 5-$HT_{1A}$, 5-$HT_{1B}$ and 5-$HT_{1D}$ receptors. A compound which is a partial agonist at the 5-$HT_{1A}$, 5-$HT_{1B}$ and 5-$HT_{1D}$ receptor must exhibit sufficient activity to increase bladder capacity and sphincter EMG activity by at least 20%. While a partial agonist of any intrinsic activity may be useful for the method of this invention, partial agonists of at least about 50% agonist effect ($E_{max}$) are preferred and partial agonists of at least about 80% agonist effect ($E_{max}$) are more preferred. Full agonists at the the $5\text{-HT}_{1A}$, $5\text{-HT}_{1B}$ and $5\text{-HT}_{1D}$ receptors are most preferred.

Suitable combined $5\text{-HT}_{1A}$, $5\text{-HT}_{1B}$ and $5\text{-HT}_{1D}$ receptor agonists include, but are not limited to, the compound of Formula I and GR46611. GR46611 is readily prepared by one of ordinary skill in the art following known processes and procedures, for example, see J. Med. Chem. (1996), 39(24) 4717–4726.

In another aspect, the present invention provides a method of treating bladder over-activity or urinary incontinence in a patient in need of such treatment, comprising administering to the patient an effective amount of a $5\text{-HT}_{1B}$ receptor agonist, a $5\text{-HT}_{1D}$ receptor agonist, or a $5\text{-HT}_{1B}$ receptor agonist in combination with a $5\text{-HT}_{1D}$ receptor agonist.

More preferably, the present invention provides a method of treating bladder over-activity or urinary incontinence in a patient in need of such treatment, comprising administering to the patient an effective amount of a $5\text{-HT}_{1B}$ receptor agonist in combination with a $5\text{-HT}_{1D}$ receptor agonist.

The term "$5\text{-HT}_{1B}$ receptor agonist", as it is used in the description of the present invention, is taken to mean a compound which is a full or partial agonist at the $5\text{-HT}_{1B}$ receptor. A compound which is a partial agonist at the the $5\text{-HT}_{1B}$ receptor must exhibit sufficient activity to increase bladder capacity and sphincter EMG activity by at least 20%. While a partial agonist of any intrinsic activity may be useful for the method of this invention, partial agonists of at least about 50% agonist effect ($E_{max}$) are preferred and partial agonists of at least about 80% agonist effect ($E_{max}$) are more preferred. A full agonist at the the $5\text{-HT}_{1B}$ receptor is most preferred.

Suitable $5\text{-HT}_{1B}$ receptor agonists include, but are not limited to, SB-216641—(N-[3-(2-dimethylamino)ethoxy4-methoxyphenyl]-2'-methyl-4'-(5-methyl-1,2,4-oxadiazol-3-yl)-(1,1'-biphenyl)-4-carboxamide), see U.S. Pat. No. 5,801,170.

The term "$5\text{-HT}_{1D}$ receptor agonist", as it is used in the description of the present invention, is taken to mean a compound which is a full or partial agonist at the $5\text{-HT}_{1D}$ receptor. A compound which is a partial agonist at the the $5\text{-HT}_{1D}$ receptor must exhibit sufficient activity to increase bladder capacity and sphincter EMG activity by at least 20%. While a partial agonist of any intrinsic activity may be useful for the method of this invention, partial agonists of at least about 50% agonist effect ($E_{max}$) are preferred and partial agonists of at least about 80% agonist effect ($E_{max}$) are more preferred. A full agonist at the $5\text{-HT}_{1D}$ receptor is most preferred.

Suitable $5\text{-HT}_{1D}$ agonists include, but are not limited to, BRL-15572— 3-[4-(3-chlorophenyl)piperazin-1-yl]-1,1-diphenyl-2-propanol), see *Eur. J. Pharmacol.*, 331(2/3), 169–174 (1997)).

The term, "a $5\text{-HT}_{1B}$ receptor agonist in combination with a $5\text{-HT}_{1D}$ receptor agonist," as it is used in the description of the present invention, is taken to mean a first compound which is a full or partial agonist at the $5\text{-HT}_{1B}$ receptor in combination with a second compound which is a full or partial agonist at the $5\text{-HT}_{1D}$ receptor.

Further, the present invention provides a method of treating bladder over-activity or urinary incontinence in a patient in need of such treatment, comprising administering to the patient an effective amount of a $5\text{-HT}_{1A}$ receptor agonist in combination with a $5\text{-HT}_{1B}$ receptor agonist and $5\text{-HT}_{1D}$ receptor agonist.

The term "$5\text{-HT}_{1A}$ receptor agonist", as it is used in the description of the present invention, is taken to mean a compound which is a full or partial agonist at the $5\text{-HT}_{1A}$ receptor. A compound which is a partial agonist at the the $5\text{-HT}_{1A}$ receptor must exhibit sufficient activity to increase bladder capacity and sphincter EMG activity by at least 20%. While a partial agonist of any intrinsic activity may be useful for the method of this invention, partial agonists of at least about 50% agonist effect ($E_{max}$) are preferred and partial agonists of at least about 80% agonist effect ($E_{max}$) are more preferred. A full agonist at the $5\text{-HT}_{1A}$ receptor is most preferred.

Suitable $5\text{-HT}_{1A}$ agonists include, but are not limited to, 8-OH-dipropyl-aminotetraline, ipsapirone (see U.S. Pat. No. 4,818,756), buspirone (see U.S. Pat. No. 3,717,634), flesinoxan (see U.S. Pat. No. 4,833,142), urapidil (see U.S. Pat. No. 3,957,786), gepirone (see U.S. Pat. No. 4,423,049), A-74283—(+,−) trans-2-(4-(3a,4,4a,6a,7,7a-hexahydro-4,7-etheno-1 H cyclobut [f] isoindol-1,3-dionyl)-butyl)-9-methoxy-2,2,2a,4,5,9b-hexahydro-1 H-benz[e]isoindol (see WO 90/06927), U-92016A—[(+)-R)-2-cyano-N,N-dipropyl-8-amino-6,7,8,9-tetrahydro-3H-benz[e]indole] (see U.S. Pat. No. 5,650,427), U-89968E, (3,4-dichlorophenyl):4-[(6-oxazol-5-ylpyridin-2-ylmethylamino)methyl]piperidin-1-yl:methanone, 4-dichlorophenyl):4-[(6-azetidinopyridin-2-ylmethylamino) methyl]piperidin-1-yl:methanone, F 11440—(4-methyl-2-[4-(4-(pyrimidin-2-yl)-piperazino)-butyl]-2H,4H-1,2,4-triazin-3,5-dione), and all dimerizations of the above compounds.

For purposes of the present invention, "a $5\text{-HT}_{1A}$ receptor agonist in combination with a $5\text{-HT}_{1B}$ receptor agonist and $5\text{-HT}_{1D}$ receptor agonist" is taken to mean at least two compounds which, in combination, are full or partial agonists at the $5\text{-HT}_{1A}$ receptor, the $5\text{-HT}_{1B}$ receptor and the $5\text{-HT}_{1D}$ receptor. For example "a $5\text{-HT}_{1A}$ receptor agonist in combination with a $5\text{-HT}_{1B}$ receptor agonist and $5\text{-HT}_{1D}$ receptor agonist" could be a compound having activity at the $5\text{-HT}_{1A}$ receptor in combination with a compound having activity at the $5\text{-HT}_{1B}$ and $5\text{-HT}_{1D}$ receptors. Alternatively, "a $5\text{-HT}_{1A}$ receptor agonist in combination with a $5\text{-HT}_{1B}$ receptor agonist and $5\text{-HT}_{1D}$ receptor agonist" could be a compound having activity at the $5\text{-HT}_{1A}$ and $5\text{-HT}_{1B}$ receptors in combination with a compound having activity at the $5\text{-HT}_{1D}$ receptor. It is to be appreciated that the invention of the present invention includes any combination that results in full or partial agonist activity at the $5\text{-HT}_{1A}$, $5\text{-HT}_{1B}$ and $5\text{-HT}_{1D}$ receptors.

It is to be appreciated that the compounds that have full or partial agonist activity at the $5\text{-HT}_{1A}$, $5\text{-HT}_{1B}$ and/or $5\text{-HT}_{1D}$ receptors, as defined above, may have activity at additional receptors. For example, a compound which has full or partial agonist activity at the $5\text{-HT}_{1B}$ and $5\text{-HT}_{1D}$ receptors may also have full or partial agonist activity at the $5\text{-HT}_{1F}$ receptor or non 5-HT receptors, such as adrenergic or cholinergic receptors.

Table II depicts the results of the binding affinity as a $K_i$ in nM or % displacement of the compound of formula I at six serotonin receptors.

TABLE II

Binding and Functional Data in Cloned Human Serotonin Receptors

| Structure | | $5\text{-}HT_{1A}$ | $5\text{-}HT_{1B}$ | $5\text{-}HT_{1D}$ | $5\text{-}HT_{1E}$ | $5\text{-}HT_{1F}$ | $5\text{-}HT_{7}$ |
|---|---|---|---|---|---|---|---|
| Formula 1 | $K_i$ | .95 | 1.7 | 1.2 | 3876 | 32.3 | 103.8 |
| | $EC_{50}$ | | .9 | .7 | | 161.5 | |
| | $E_{max}$ | | 88.2 | 93.4 | | 95.5 | |
| | $K_b$ | | | | | | |
| | | | Agonist | Agonist | | Agonist | |

Table II reveals that the compound of formula I is an agonist at the $5\text{-}HT_{1A}$, $5\text{-}HT_{1B}$ and $5\text{-}HT_{1D}$ receptors.

Accordingly, the present invention also provides a method of treating bladder over-activity or urinary incontinence in a patient in need of such treatment, comprising administering to the patient an effective amount of a compound of formula I.

The terms "treating" or "treat" as used herein include the generally accepted meaning which encompasses prohibiting, preventing, restraining, and slowing, stopping, or reversing progression, severity, of a resultant symptom. As such, the methods of this invention encompass both therapeutic and prophylactic administration.

As used herein, the terms "bladder over-activity" and "detrusor over-activity" refer to activity of the urinary bladder that causes or presents symptoms of urinary frequency, urinary urgency, nocturia, and/or urinary incontinence. The term "urinary frequency" as used herein refers to a need for frequent emptying of the bladder. The term "urinary urgency" refers to an urgent sensation of an impending void that may not be controllable. The term "nocturia" as used herein is defined as awakening frequently during sleep to void. The conditions associated with bladder over-activity include, but are not limited to, bladder hyperactivity, bladder hyperreflexia, unstable bladder, neurogenic bladder, uninhibited bladder contractions. For purposes of the present invention, it is understood that the terms "bladder" and "detrusor" are interchangeable.

As used herein, the term "urinary incontinence" refers to the involuntary voiding of any quantity of urine resulting from bladder activity by the patient from the patient's body.

The term "urge urinary incontinence" for purposes of this invention refers to the involuntary voiding of any quantity of urine resulting from bladder activity by the patient from the patient's body. Urge incontinence is caused by excessive intra-bladder pressure.

The term "stress urinary incontinence" for purposes of the present invention refers to involuntary voiding of any quantity of urine resulting from a weak urethral sphincter by the patient from the patient's body. A weak urethral sphincter that allows the leakage or urine during a cough, laugh, or sneeze in the absense of bladder over-activity results in stress incontinence.

Urinary incontinence is a manifestation of the failure of control of the muscles of the urinary sphincter and of the bladder. Those muscles are in balance, when the system is operating properly. The urinary sphincter should be sufficiently strong to hold back the pressure exerted by the muscles of the bladder, except when the subject consciously relaxes the sphincter in order to urinate. Incontinence results when the pressure within the bladder is too great, as a result of excessive force exerted by the muscles of the bladder or when the urinary sphincter is too weak to hold back the normal intra-bladder pressure. Incontinence is broadly classified as urge incontinence and stress incontinence. Patients often are seen with components of both urge and stress incontinence, a condition that is referred to herein as "mixed urinary incontinence" or "mixed incontinence". It is understood that urge incontinence, stress incontinence and mixed incontinence fall within the scope of the term urinary incontinence or incontinence.

The methods of the present invention are used to treat and control bladder over-activity and urinary incontinence, either alone or in combination, in patients of any age in need of such treatment. The methods of the present invention are used to treat and control urinary incontinence of any one, or all of the stress, urge, and mixed types, in patients of any age in need of such treatment. The cause of the bladder over-activity or urinary incontinence is not critical to the benefit of the present invention. For example, incontinence caused by deterioration of the central nervous system, the peripheral nervous system, the muscles of the bladder or urethra, and infections of bladder or urethra are all effectively treated by the present method.

The types of bladder over-activity and urinary incontinence which have resulted from or have been caused by various neurological disorders, such as Parkinson's disease, multiple sclerosis, spinal cord injury, stroke, and Alzheimer's disease are effectively treated by the present method. Furthermore, bladder over-activity and incontinence which is caused by or has resulted from various disorders localized to the lower urinary tract, such as prostatitis, prostatodynia, urethritis, detrusor instability, interstitial cystitis, urinary tract infection, outlet obstruction, benign prostate hyperplasia, diabetes, or vulvodynia are effectively treated by the present method. Still further, bladder over-activity and urinary incontinence brought about by pelvic surgery, radiation therapy of the pelvis viscera, or anatomical changes in the geometry of the bladder and urethra, urethral deterioration as a result of cessation of estrogen production, and bladder hyperactivity are all effectively treated. Finally, bladder over-activity and incontinence which are idiopathic are all treated by the method of the present invention.

It will be demonstrated by the examples that follow that the methods of the present invention have the ability to increase the effective volume of the bladder, and simultaneously to increase the contractility and nervous system control of the muscles which manage the urethra. Accordingly, it is clear that the present invention controls both bladder over-activity and incontinence, by increasing the effective volume of the bladder and decreasing involuntary muscular activity around the bladder. Furthermore, the present invention controls stress incontinence by increasing control of the urethral sphincter and improving the tone of the urethral musculature.

Adult female cats were anesthetized with alpha chloralose (50–75 mg/kg i.v.) One catheter was inserted into the carotid artery for measuring systemic blood pressure and heart rate. A second catheter was inserted in the radial vein for administering drugs. Following a midline laparotomy, the bladder was cannulated through the dome to allow infusion of fluids and recording of intravesical pressure. The urethra remained patent to allow expulsion of fluids during reflex micturition.

Transvesical cystometrograms (CMGs) were recorded by emptying the bladder, beginning infusion (0.5 ml/min) with saline, and noting the volume at which fluid release and bladder contraction occurred (i.e. micturition). This volume is defined as bladder capacity. EMG activity was recorded from the periurethral musculature with bipolar hook electrodes placed within 0.5 cm of the urethral meatus via an intravaginal approach. After establishing bladder capacity and EMG activity under conditions of saline infusion, the infusion cannula was switched to infuse 0.5% acetic acid solution and cystometry repeated.

Following cystometry, the bladder was allowed to continuously fill, which produced rhythmic bladder contractions accompanied by fluid release. During this time of rhythmic bladder activity, vehicle or drug was administered. Within 5 minutes, the bladder was emptied; another CMG was performed, and bladder capacity and EMG activity were again measured. The bladder was then continuously filled to produce rhythmic contractions with fluid release, and the frequency of these rhythmic contractions was measured over a fifteen minute period to record drug effects on contraction frequency. This procedure was repeated with increasing doses of drug to produce a cumulative dose response curve.

GR46611 and GR127935 were dissolved with addition of a few drops of acetic acid into saline. All other drugs were dissolved in saline.

Figure 1B:
Figure 1B:
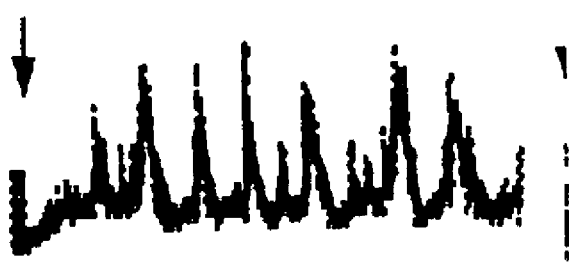
Figure 2A:
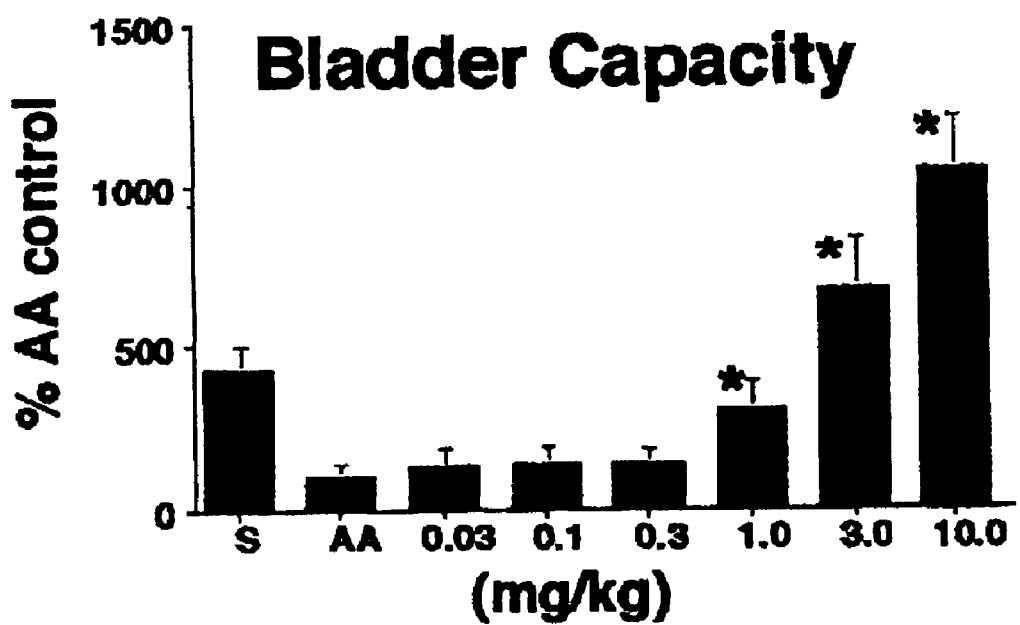
FIGS. 2A, 2B, and 2C—The effect of the administration of zolmitriptan on bladder capacity, bladder contraction frequency, and external urethral sphincter EMG activity.
Figure 2B:
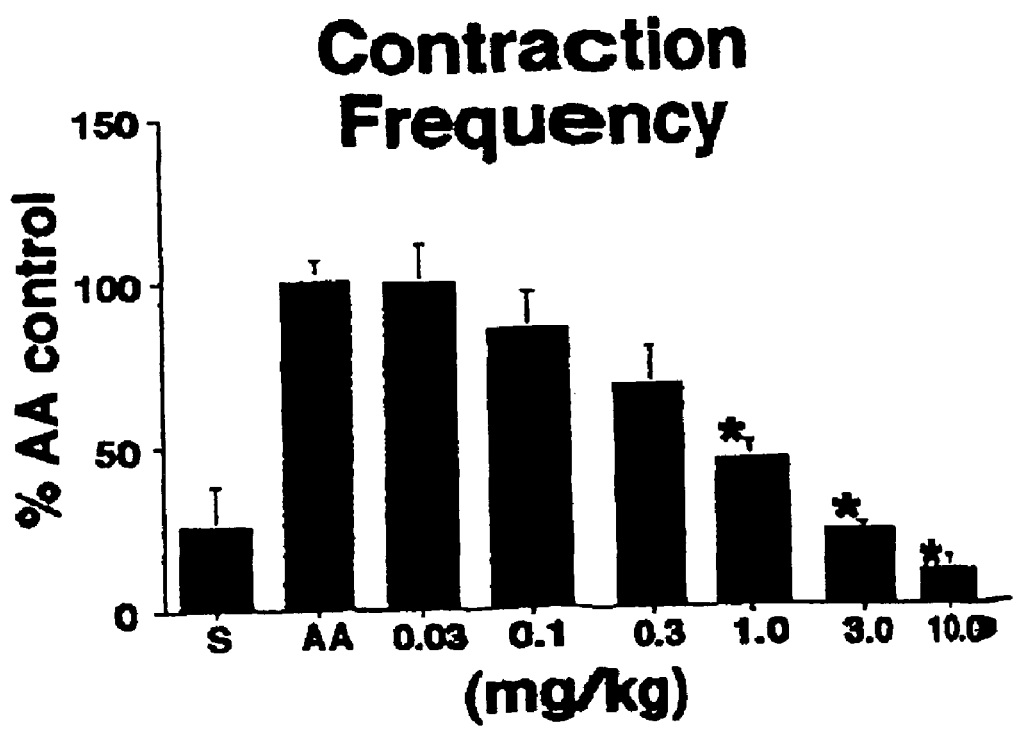
Figure 2C:
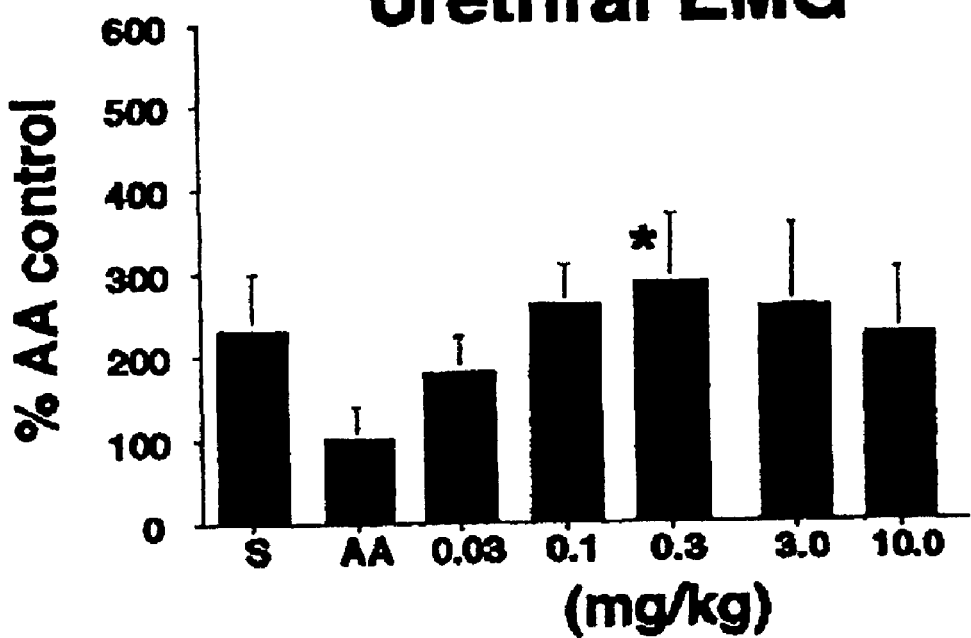
Figure 3A:
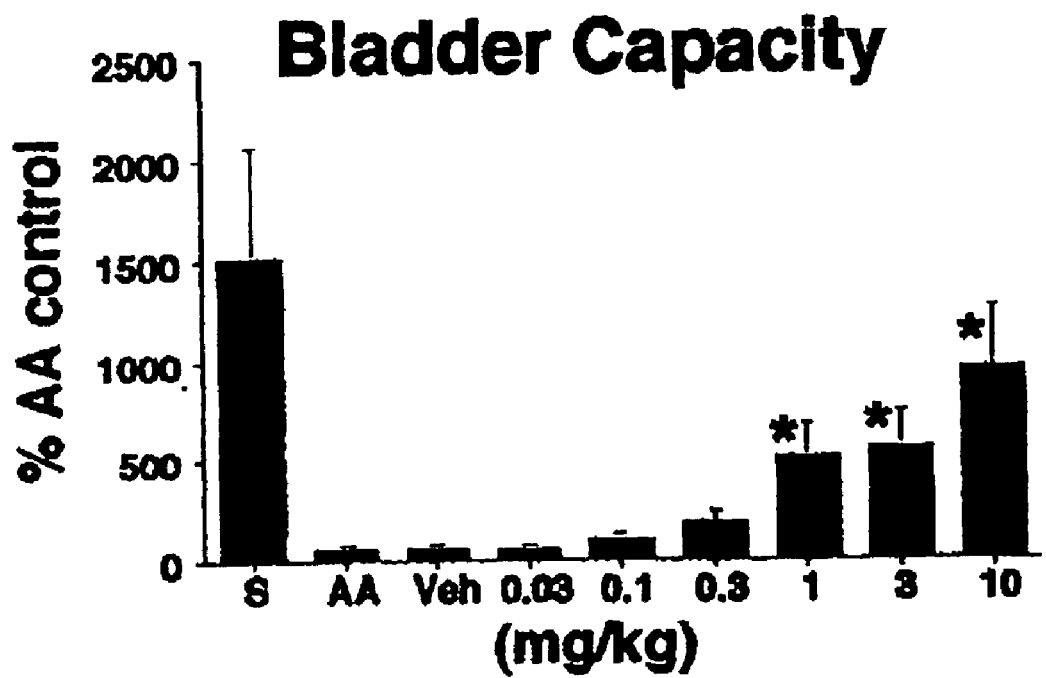
FIGS. 3A, 3B, and 3C—The effect of the administration of GR127935 on bladder capacity, bladder contraction frequency, and external urethral sphincter EMG activity.
Figure 3B:
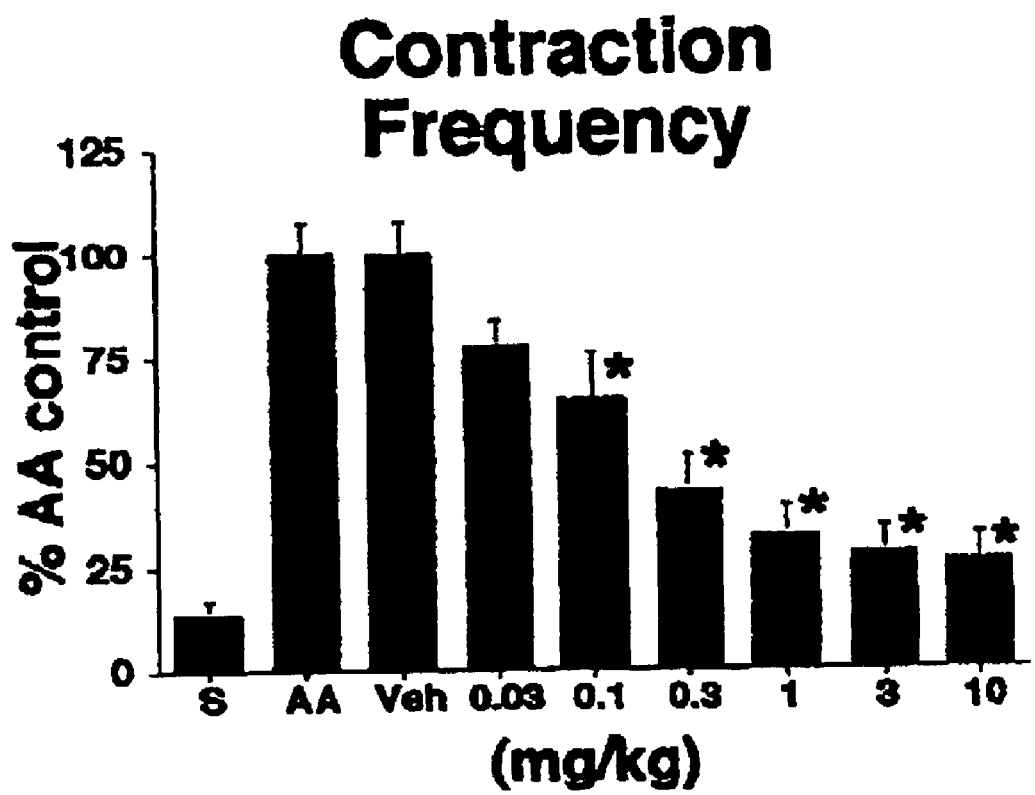
Figure 3C:
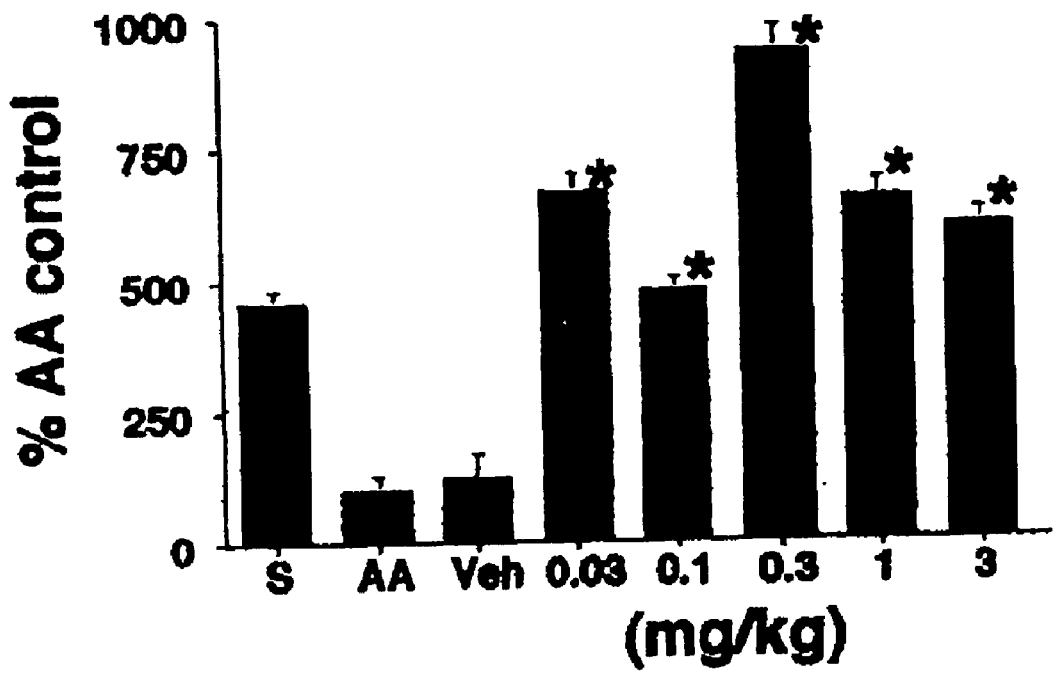
Figure 4A:
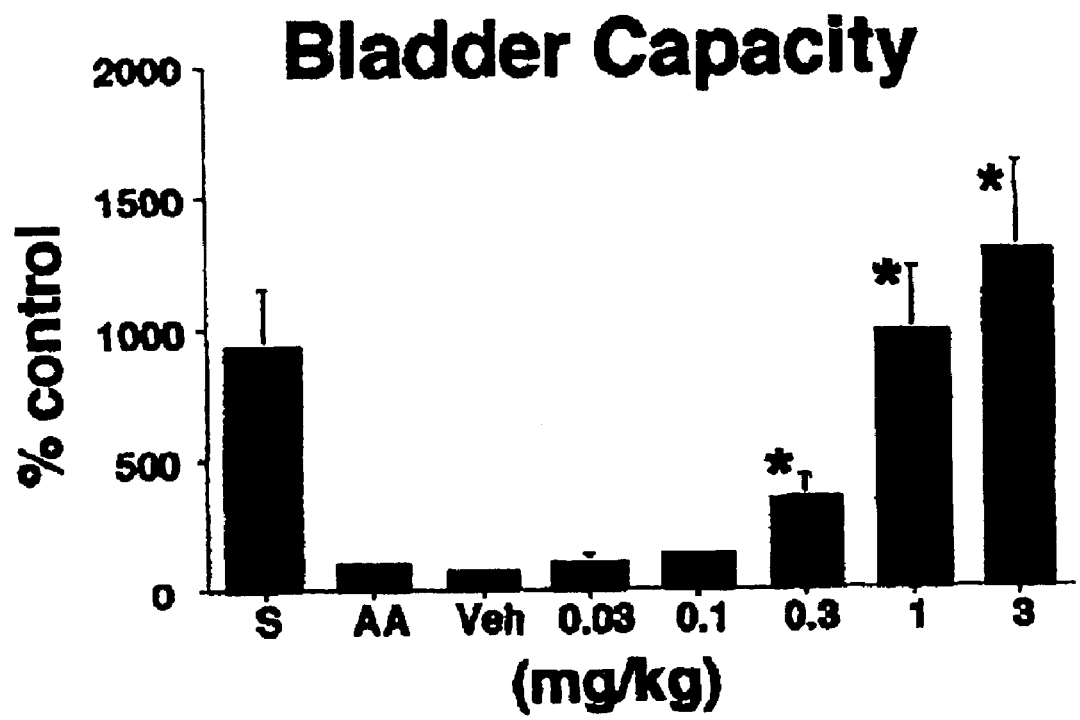
FIGS. 4A, 4B, and 4C—The effect of the administration of GR46611 on bladder capacity, bladder contraction frequency, and external urethral sphincter EMG activity.
Figure 4B:
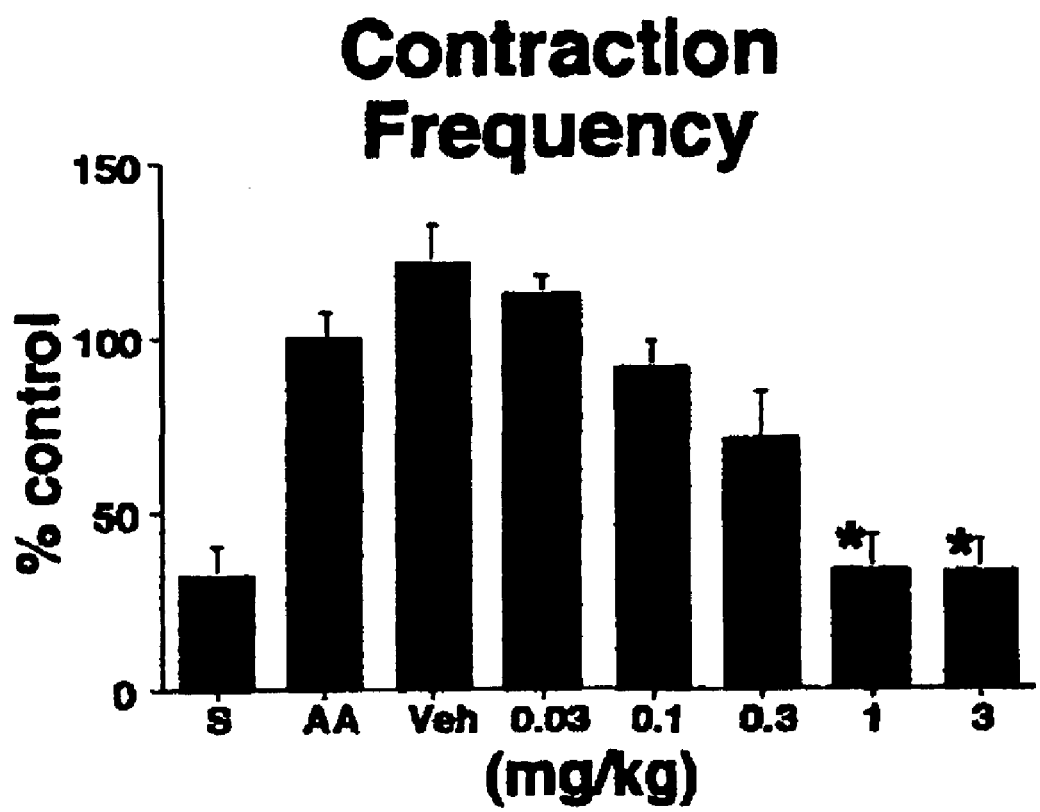
Figure 4C:
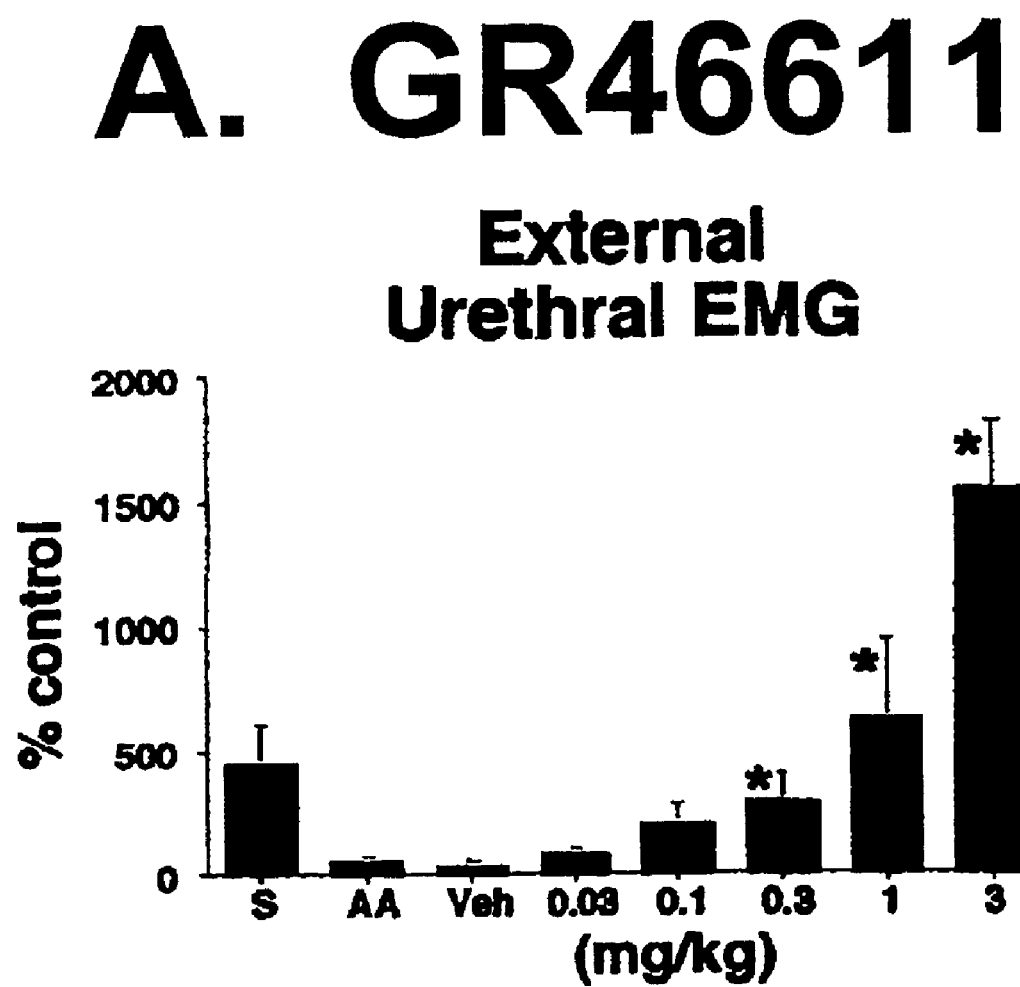
Figure 5A:
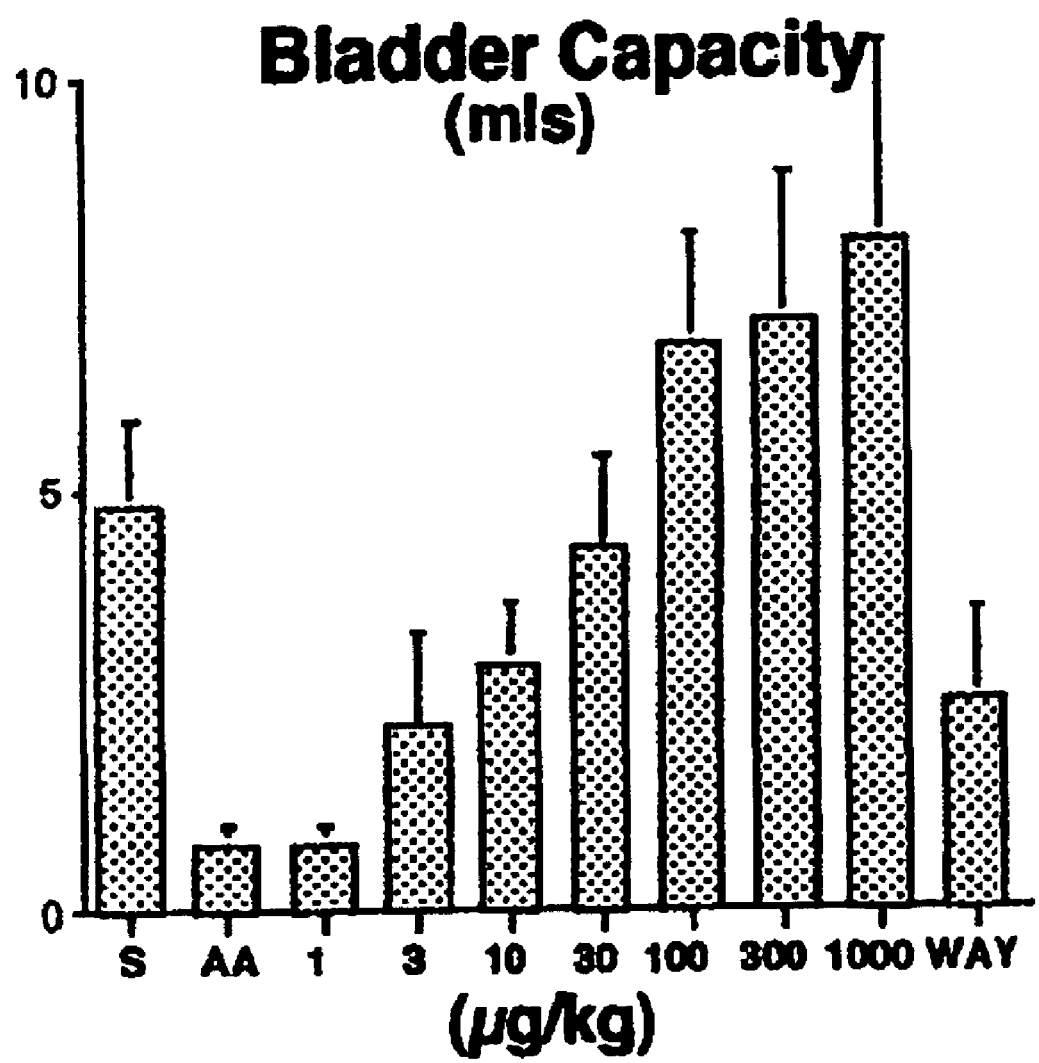
FIGS. 5A, 5B, and 5C—The effect of the administration of LY217101 on bladder capacity, bladder contraction frequency, and external urethral sphincter EMG activity.
Figure 5B:
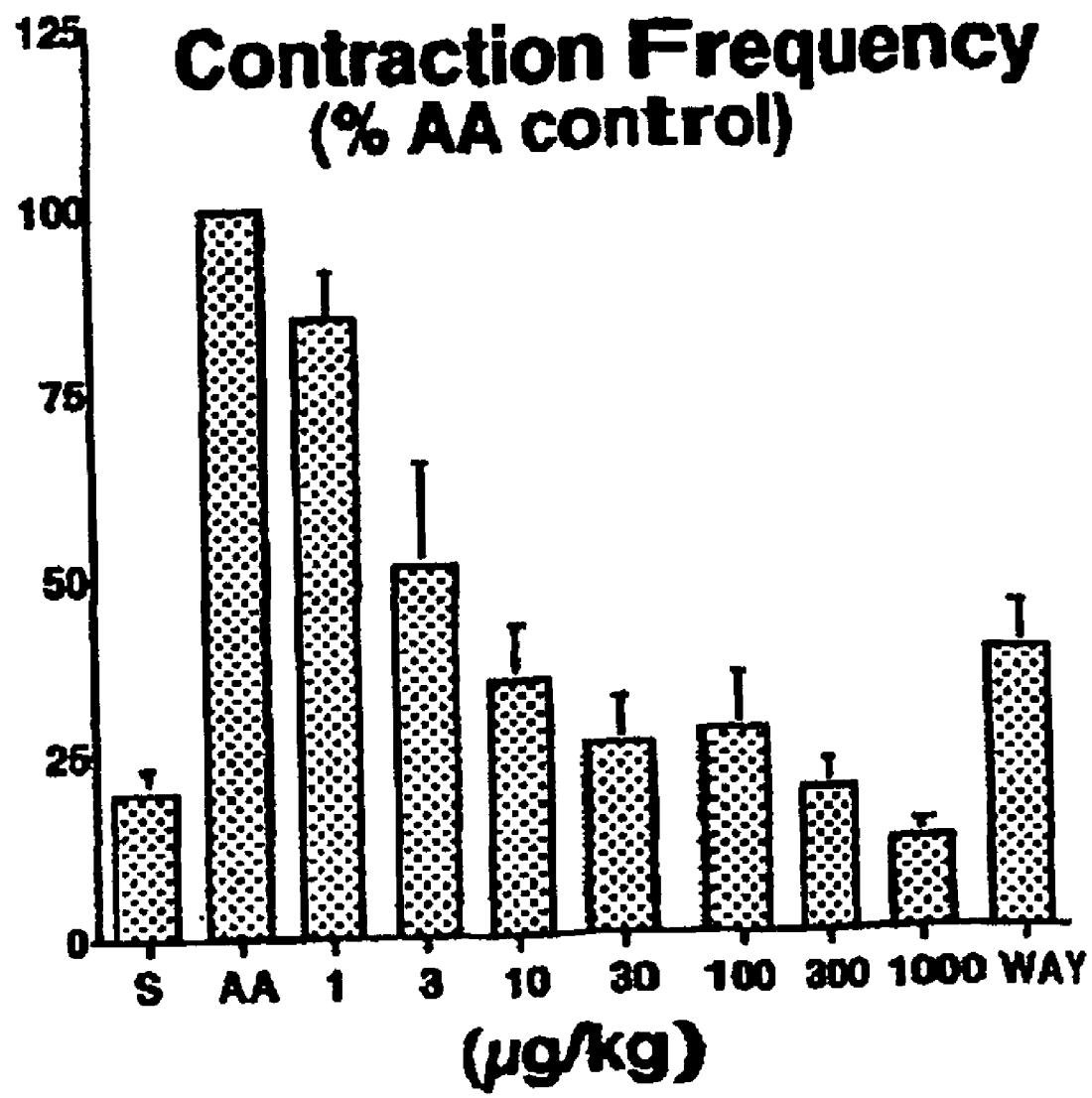
Figure 5C:
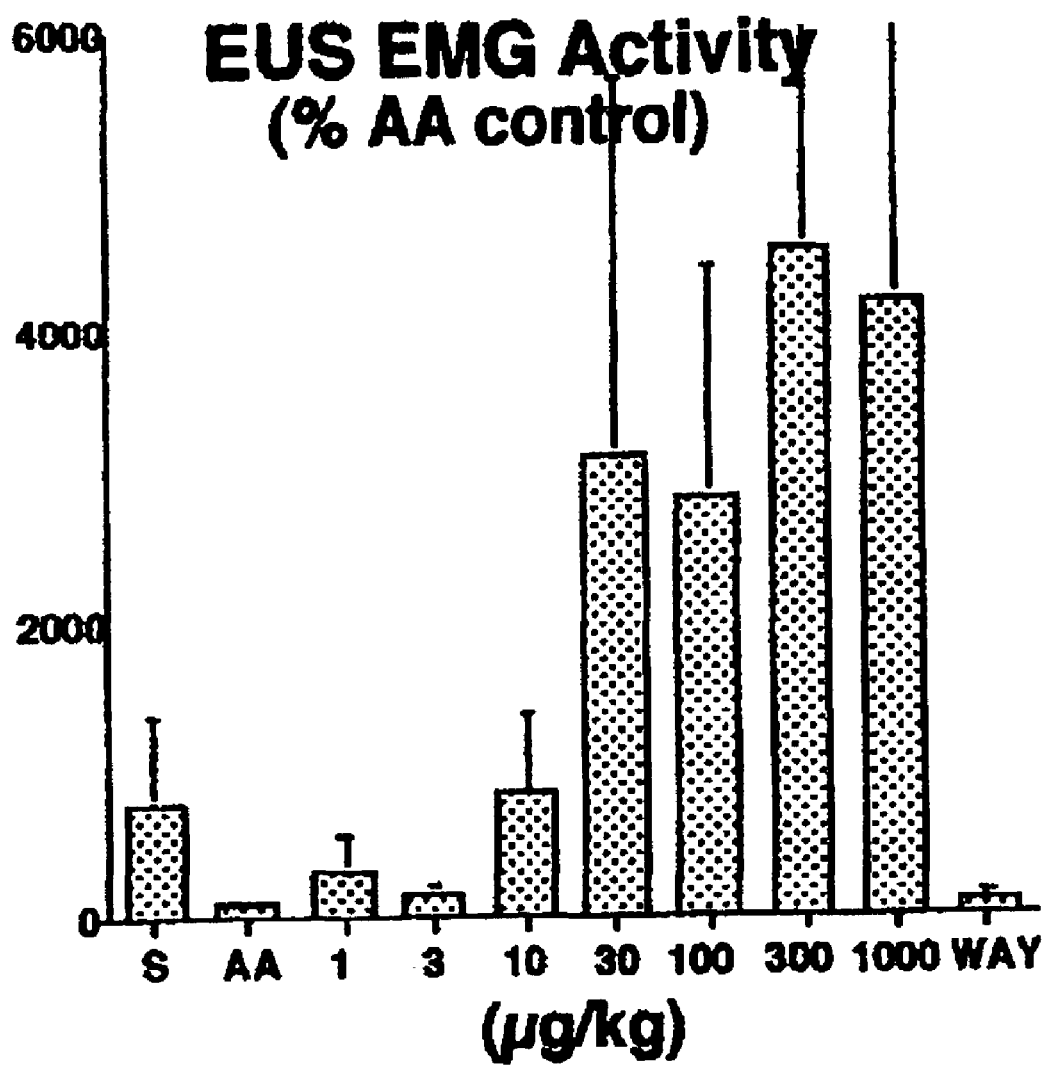
Figure 6A:
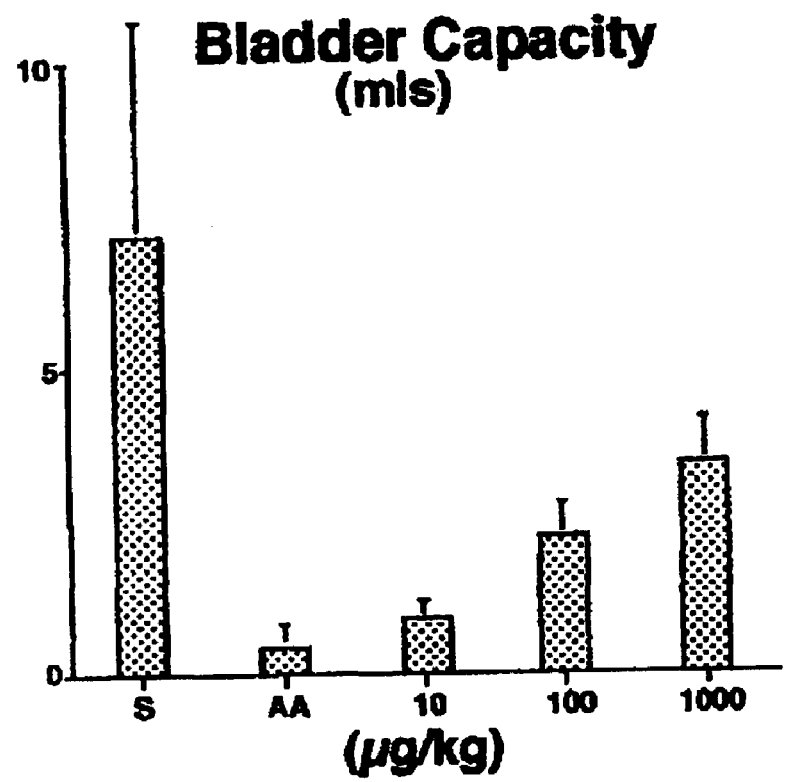
FIGS. 6A, 6B, and 6C—The effect of the administration of LY217101 after WAY100635 on bladder capacity, bladder contraction frequency, and external urethral sphincter EMG activity.
Figure 6B:
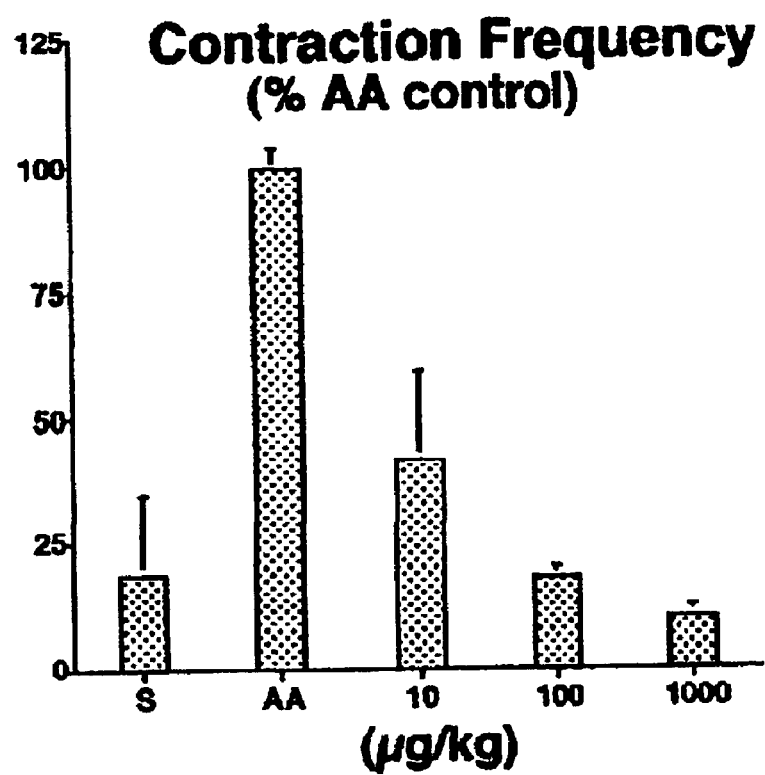
Figure 6C:
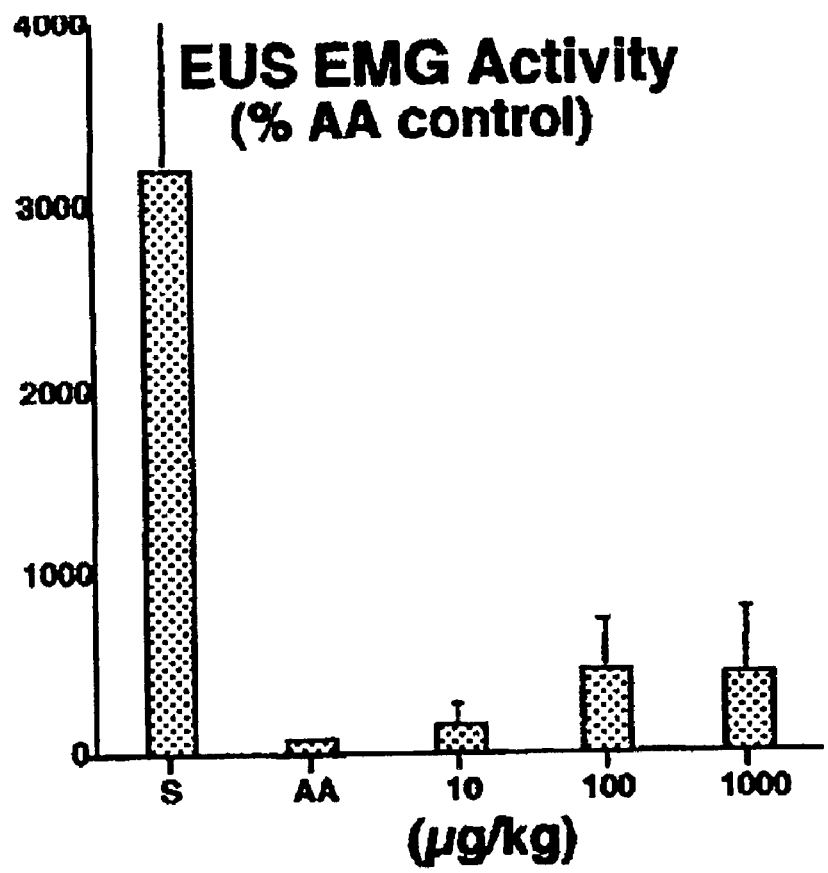

Under control conditions (FIG. 1A), large (30–50 cm $H_2O$), rapid increases in intravesical pressure, i.e. micturition contractions mediated by a central reflex pathway, were recorded after infusion of approximately 5 ml saline into an initially empty bladder. The volume at which these micturitions contractions occur define bladder capacity. Upon switching to infusion of acetic acid (FIG. 1B); bladder capacity, contraction amplitude, and contraction duration were reduced, while the contraction frequency was increased. Very little peri-urethral EMG activity was recorded during infusion of saline and decreased slightly during infusion of acetic acid (FIGS. 2 and 3). The small amount of EMG activity that was recorded in control periods occurred during, or immediately after, a bladder contraction and was composed of phasic bursts of activity (each burst lasting 150–300 msec) separated by short (150–350 msec) periods of quiescence.

Figure 1C:
Figure 7A:
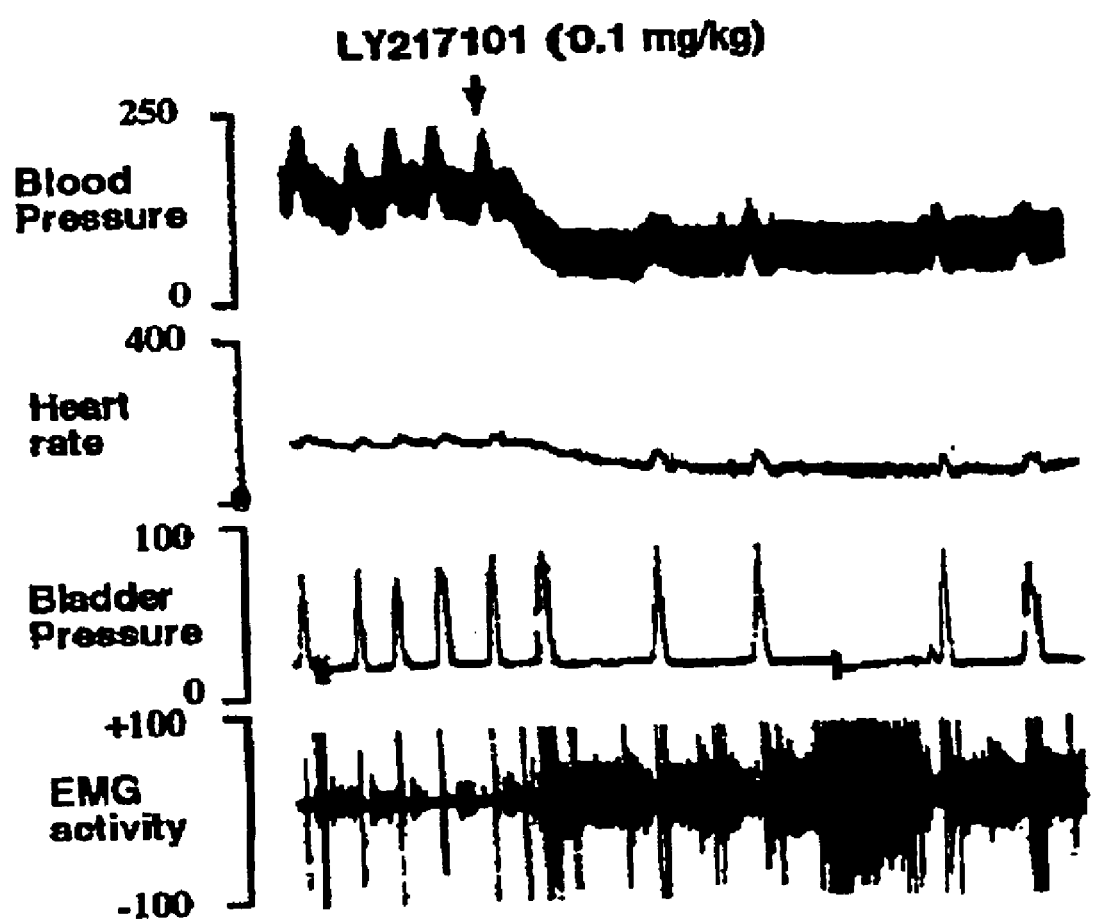
Figure 7C:
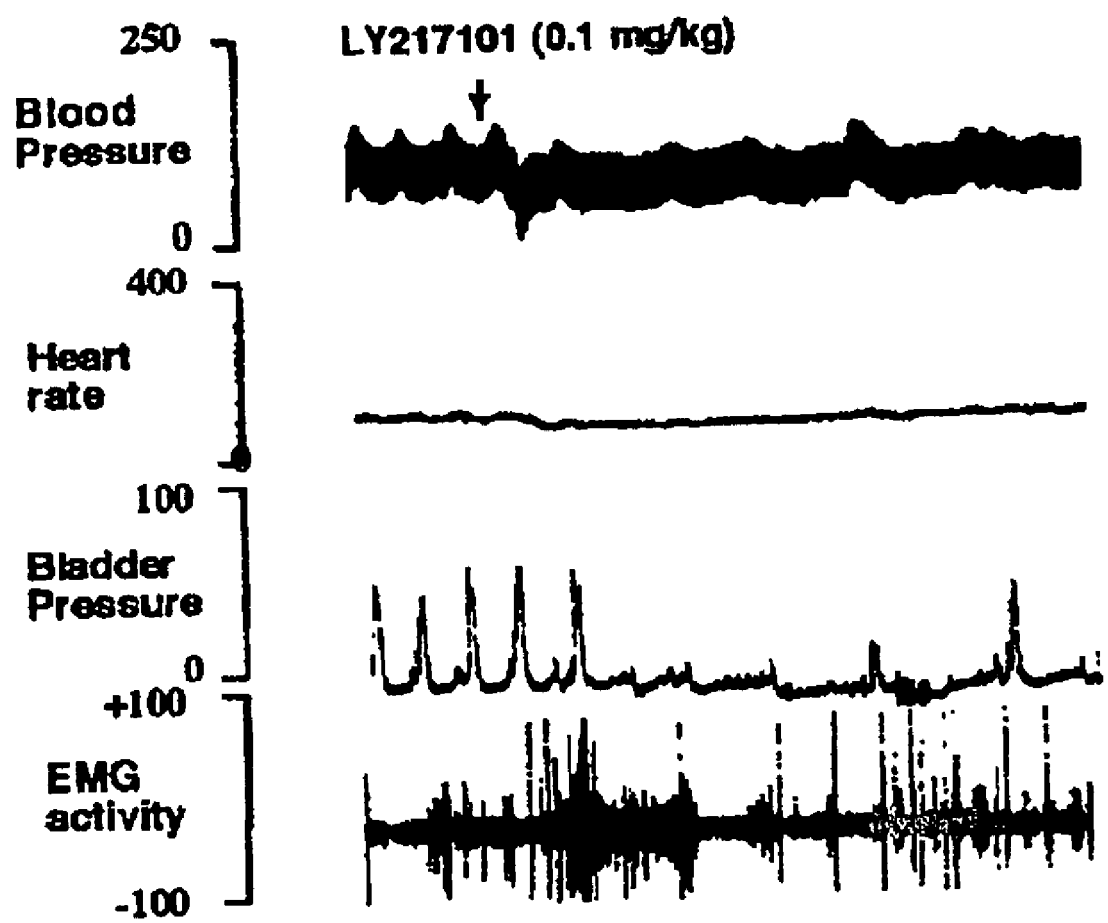

Administration of either a combined 5-$HT_{1B}$ and 5-$HT_{1D}$ receptor agonist, such as zolmitriptan and GR127935, or a combined 5-$HT_{1A}$, 5-$HT_{1B}$ and 5-$HT_{1D}$ receptor agonist, such as GR46611 and LY217101 produced dose-dependent increases in bladder capacity (FIGS. 2A, 3A, 4A and 5A). The increase in bladder capacity was not accompanied by changes in the amplitude or duration of the contractions upon reaching micturition threshold volumes (FIGS. 1C and 7A). Administration of zolmitriptan, GR127935, GR46611 and LY217101 also reduced the frequency of micturition contractions (FIGS. 2B, 3B, 4B and 5B). Administration of zolmitriptan, GR127935, GR46611 and LY217101 also increase external urethral sphincter ("EUS") electromyographic ("EMG") activity (FIGS. 1C, 2C, 3C, 4C, 5C and 7A).

WAY100635, a 5-$HT_{1A}$ receptor antagonist, partially reversed the hypotension, bradycardia, decrease in contraction frequency and increase in EMG activity induced by the administration of the compound of Formula I (FIG. 7B). Although administration of LY217101 after WAY 100635 no longer produces hypotension, bradycardia or increase in EMG activity, the administration of LY217101 after WAY100635 continued to reduce the frequency of micturition contractions and to increase bladder capacity (FIGS. 6A, 6B, 6C and 7C).

The results show that administration of either a combined 5-$HT_{1B}$ and 5-$HT_{1D}$ receptor agonist or a combined 5-$HT_{1A}$, 5-$HT_{1B}$ and 5-$HT_{1D}$ receptor agonist increases bladder capacity. The increase in bladder capacity indicates utility for the treatment of bladder over-activity and incontinence.

Additionally, the results show that administration of either a combined 5-$HT_{1B}$ and 5-$HT_{1D}$ receptor agonist or a combined 5-$HT_{1A}$, 5-$HT_{1B}$ and 5-$HT_{1D}$ receptor agonist increases EUS EMG activity. The increase in EMG activity indicates utility for the treatment of stress urinary incontinence.

Finally, the results show that administration of either a combined 5-$HT_{1B}$ and 5-$HT_{1D}$ receptor agonist or a combined 5-$HT_{1A}$, 5-$HT_{1B}$ and 5-$HT_{1D}$ receptor agonist had no effect on the magnitude of the bladder contraction once it had reached micturition occurred as efficiently after treatment as it had before treatment. This is important in light of the fact that current bladder over-activity and incontinence medicines, primarily anticholinergics, cause decreased efficiency of micturition and increases in residual urine due to compromise of bladder contractile force.

As used herein the term "patient" refers to a mammal, such as a rat, guinea pig, mouse, cat, dog or human. It is understood that the preferred patient is a human.

Based on standard clinical and laboratory tests and procedures, an attending diagnostician, as a person skilled in the art, can readily identify those patients who are in need of treatment for bladder over-activity or urge urinary incontinence.

As used herein the term "effective amount" refers to the amount or dose of the agonist compound or agonist compounds of the present invention, such as a compound of formula I, which provide the desired effect in the patient under diagnosis or treatment.

The term "agonist compound" or "agonist compounds" as used herein includes, a combined 5-$HT_{1B}$ and 5-$HT_{1D}$ receptor agonist, a combined 5-$HT_{1A}$, 5-$HT_{1B}$ and 5-$HT_{1D}$ receptor agonist, a 5-$HT_{1B}$ receptor agonist in combination with a 5-$HT_{1D}$ receptor agonist, and a 5-$HT_{1A}$ receptor agonist in combination with a 5-$HT_{1B}$ receptor agonist and 5-$HT_{1D}$ receptor agonist.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the degree of or involvement or the severity of the disease; the response of the individual patient; the particular agonist or agonists administered; the mode of administration; the bioavailability characteristics of the preparation administered; the dose regimen selected; the use of concomitant medication; and other relevant circumstances.

An effective amount of a compound of formula I is expected to vary from about 0.001 micrograms per kilogram of body weight per day (mg/kg/day) to about 100 mg/kg/day. Preferred amounts are expected to vary from about 0.001 mg/kg/day to about 10 mg/kg/day. Especially preferred amounts are expected to vary from about 0.01 mg/kg/day to about 1 mg/kg/day.

It is to be appreciated that the agonist compounds of the present invention can be administered alone or in combination. For example, a combined $5\text{-}HT_{1B}$ and $5\text{-}HT_{1D}$ receptor agonist is administered alone. However, a $5\text{-}HT_{1B}$ receptor agonist in combination with a $5\text{-}HT_{1D}$ receptor agonist is administered as a combination.

Generally, a combination of the agonist compounds of the present invention is created by choosing a dosage of each agonist according to the spirit of the above dosage guidelines and administering each agonist in any manner which provides effective levels of the two compounds in the body at the same time. They may be administered together, in a single dosage form, or may be administered separately.

It is particularly preferred, however, for the adjunctive combination to be administered as a single pharmaceutical composition, and so pharmaceutical compositions incorporating a combination of agonists are important embodiments of the present invention. Such compositions may take any physical form, which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

In effecting treatment of a patient suffering from bladder over-activity or urinary incontinence, the agonist compounds of the present invention, such as the compound of formula I, can be administered in any form or mode which makes the compound bioavailable in effective amounts, including oral and parenteral routes. For example, compounds of formula I can be administered orally, subcutaneously, percutaneously, intramuscularly, intravenously, transdermally, intranasally, rectally, and the like. Oral administration is generally preferred.

One skilled in the art of preparing formulations can readily select the proper form and mode of administration depending upon the particular characteristics of the agonist compound selected, the disease state to treated, the severity of the disease, and other relevant circumstances. The route of administration may be varied in any way, limited by the physical properties of the drugs and the convenience of the patient and the caregiver.

It is to be appreciated that when the agonist compounds of the present invention are administered in combination, each agonist compound may be administered by a different route. For example, one of the drugs may be administered by one route, such as oral, and the other may be administered by a second route, such as transdermal.

The agonist compounds of the present invention, such as the compound of formula I can be administered alone or in the form of a pharmaceutical composition in combination with pharmaceutically acceptable carriers or excipients, the proportion and nature of which are determined by the solubility and other chemical properties of the compound selected, the chosen route of administration, and standard pharmaceutical practice. The agonist compounds of the invention, while effective themselves, may be formulated and administered in the form of their pharmaceutically acceptable salts for purposes of stability, convenience of crystallization, increased solubility, and the like.

In another embodiment, the present invention provides compositions comprising a compound of formula I in admixture or otherwise in association with one or more inert carriers. These compositions are useful, for example, as a convenient means of making bulk shipments, or as pharmaceutical compositions.

More particularly, the present invention provides a pharmaceutical composition comprising an effective amount of a compound of formula I and one or more pharmaceutically acceptable diluents or carriers.

The pharmaceutical compositions are prepared in a manner well known in the pharmaceutical art. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The term "active ingredient" refers to, for example, a compound of formula I.

In general all of the compositions are prepared according to methods usual in pharmaceutical chemistry. A group of typical formulae of compositions will be mentioned below, but the principles of such formulations are so well known that no detailed discussion will be provided.

Formulation 1

Hard gelatin capsules are prepared using the following ingredients

| | Quantity (mg/capsule) |
|---|---|
| Active Ingredient | 5 |
| Starch, dried | 445 |
| Magnesium stearate | 10 |
| Total | 460 mg |

Formulation 2

A tablet is prepared using the ingredients below:

| | Quantity (mg/capsule) |
|---|---|
| Active Ingredient | 10 |
| Cellulose, microcrystalline | 640 |
| Silicon dioxide, fumed | 10 |
| Stearic acid | 5 |
| Total | 665 mg |

The components are blended and compressed to form tablets each weighing 665 mg.

The following examples further illustrate the invention and represent a typical syntheses of the compounds of formula I as described generally above. The reagents and starting materials are readily available to one of ordinary skill in the art. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "δ" refers to part per million down-field from tetramethylsilane; "THF" refers to tetrahydrofuran; "de" refers to diasteromeric excess; "i-PrOH" refers to isopropyl alcohol; "EtOH" refers to ethanol; "MeOH" refers to methanol; and "DMF" refers to N,N-dimethylformamide;

EXAMPLE 1

Preparation of 1-(2-m-methanesulfonamidophenylethyl)-4-(m-trifluoromethylphenyl)piperazine oxalate

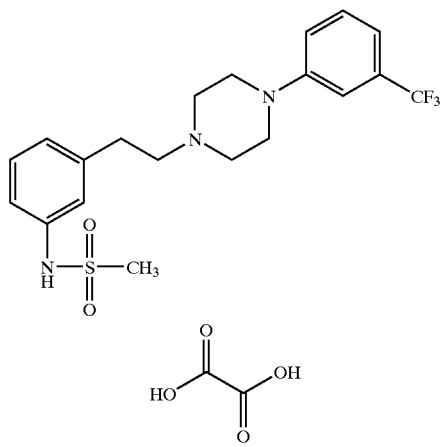

Scheme I, step A: 36.2 g (0.2 mole) of 3-Nitrophenylacetic acid (1) was stirred in 400 mL toluene at ambient temperature while 87.0 mL (1.0 mole) of Oxalyl chloride was added dropwise. After the addition was complete, the reaction was stirred for 1 hour at ambient temperature. The solution was slowly heated until an exothermic reaction occurred (approx. 56° C.). The external heat source was then removed until the reaction subsided. Continued heating at reflux temperature (approx. 95° C.) for 2 additional hours. Evaporation of the solution gave the acid chloride intermediate as a viscous oil. This crude intermediate was dissolved in 500 mL acetone and this solution added dropwise to a stirred mixture containing: 21.2 g (0.2 mole) Sodium carbonate, 46.0 g (0.2 mole) N-(α,α,α-trifluoro-m-tolyl) piperazine (2), 250 mL water and 250 mL acetone. The temperature was kept below 30° C. with occasional cooling. This mixture was stirred at ambient temperature for 16 hours. The acetone was evaporated from the reaction mixture and the remaining solution extracted with diethyl ether three times. The extracts were washed consecutively with water, 2N HCl solution and brine. After drying with sodium sulfate and filtering, the solution was evaporated to 69.9 g (97%) of the amide (3) as a viscous oil which was sufficiently pure for use in the next reaction.

Scheme I, step B: A solution of 69.7 g (0.19 mole) of amide (3) dissolved in 700 mL tetrahydrofuran (THF) was added dropwise to 380 mL (0.38 mole) of a 1M Borane/THF solution. The temperature rose to 30° C. during this addition. This resulting solution stirred at ambient temperature for 16 hours. After cooling to 5° C., 216 mL of a 2N HCl solution was added dropwise. The THF was evaporated from the resulting solution. Added 650 mL of a 6N HCl solution to the remaining residue and heated this mixture at approximately 90° C. for one hour. Cooled and basified (pH>12) with a 5N sodium hydroxide solution. Extracted this mixture 3 times with diethyl ether. The extracts were washed with water and brine. After drying over sodium sulfate and filtering, the solution was evaporated to provide 64.3 g of piperazine (4) as an orange oil. The addition of one equivalent of p-toluenesulfonic acid to an ethyl acetate solution of the above oil precipitated the tosylate salt. Recrystallization of this salt from ethanol provided 51.3 g (49%) of yellow plates. mp 215°–217° C. Anal. C,H,N.

Scheme I, step C: A solution of 19.0 g (0.05 mole) of piperazine (4), as the free base, in 225 mL ethanol was hydrogenated over 2.5 g of Raney nickel at 60 PSI and ambient temperature for 2 hours. The solution was filtered and then evaporated to a solid. Recrystallization from hexanes provided 10.4 g (59%) of the amine (5) as colorless crystals. mp 70°–72° C. Anal. C,H,N. $^1$H NMR (DMSO-d$_6$): δ 2.45–2.65 (m, 8H). 3.17–3.27 (m, 4H), 4.93 (s, 2H), 6.32–6.45 (m, 3H), 6.85–7.45 (m, 5H).

Alternatively, Scheme I, Step C can be performed as follows: Piperazine (4) was dissolved in ethanol (100%, 60 mL) and divided in four portions (3×30 mL and 1×15 mL). Each of the portions were further dissolved with ethanol (100%, 100 mL), and Pd/C (10%, 1.5 g for the 1$^{st}$ three and 1.0 g for the last portion) was added. The resulting solution was placed under H$_2$ (60 psi) with additional H$_2$ added as needed to maintain 60 psi throughout the reduction. H$_2$ was consumed for 20.5, 21.5, 17.5, and 4 h for each portion respectively. The reaction was monitored by positive ion mass spectroscopy until completion. The portions were filtered through Celite® and rinsed with absolute ethanol. The portions were combined and concentrated to an oil under vacuum, to yield amine (5) (52.27 g, 99%).

Scheme I, step D: To a cold solution (<10° C.) of 1.4 g (4.0 mmole) of amine (5) dissolved in 12.5 mL pyridine, was added dropwise 0.38 mL (5.0 mmole) of methanesulfonyl chloride. The resulting solution was stirred at ambient temperature for 16 hours. The solution was poured onto 60 mL cold water and extracted 3 times with diethyl ether. The extracts were washed with water and brine. After drying over sodium sulfate and filtering, the solution was evaporated to 2.13 g of an orange oil. Flash chromatography (dichloromethane/methanol, 100/3, silica gel) provided 1.83 g of 1-(2-m-methanesulfonamidophenylethyl)-4-(m-trifluoromethylphenyl)piperazine.

Alternatively, Scheme I, Step D can be performed as follows: Amine (5) (47.25 g. 0.135 mol) in anhydrous pyridine (420 mL) was cooled to 5° C. Methanesulfonyl chloride (13 mL, 0.169 mol) was added dropwise over 30 min while maintaining 5° C. The solution was allowed to warm to ambient temperature and stirred for 16 h. The solution was split into two portions (250 mL) and extracted separately. Each portion was poured into H$_2$O (1 L, 0° C.) and extracted with Et$_2$O (250 mL,×3). The combined Et$_2$O layers were washed twice with H$_2$O and brine. The washed Et$_2$O layers were dried over Na$_2$SO$_4$. The separated portions were recombined, and the solvent was removed under vacuum to yield an oil. The oil was treated 3 times with toluene (250 mL) and dried under vacuum to help remove residual pyridine. Crude 1-(2-m-methanesulfonamidophenylethyl)-4-(m-trifluoromethylphenyl)piperazine was obtained (55.9 g, 97%).

The crude 1-(2-m-methanesulfonamidophenylethyl)-4-(m-trifluoromethylphenyl)piperazine was split into 4 batches and flash chromatographed on four silica gel columns. The 1$^{st}$ column of 1-(2-m-methanesulfonamidophenylethyl)-4-(m-trifluoromethylphenyl)piperazine (9.95 g) and silica gel (550 g) was eluted with a gradient of MeOH running from 1% to 5%, with 0.1% NH$_4$OH, the balance being methylene chloride. The 2$^{nd}$ column of 1-(2-m-methanesulfonamidophenylethyl)-4-(m-trifluoromethylphenyl)piperazine (10.5 g) and silica gel (0.55 kg) was eluted with methylene chloride: MeOH:NH$_4$OH (96.5:3:0.5). The third and fourth columns were packed with silica gel (1.4 kg) and were loaded with 1-(2-m-methanesulfonamidophenylethyl)-4-(m-trifluoromethylphenyl)piperazine (14.64 g and 20.03 g). The third column had a gradient of 3% to 5% MeOH and the fourth was run with a gradient of 3.5% to 4% MeOH, both with 0.5% NH$_4$OH, and the remainder being CH$_2$Cl$_2$. The columns were followed by TLC with a mobile phase of with methylene chloride: MeOH:NH$_4$OH (94:5:1), and visualized with UV (254 nm) and ninhydrin stain. The fractions of greater than 99% purity were combined to give 1-(2-m-methanesulfonamidophenylethyl)-4-(m-trifluoromethylphenyl)piperazine (16.46 g).

Formation of the oxalate salt and recrystallization from ethyl acetate/methanol gave 1.66 g (80%) of the final title compound, 1-(2-m-methanesulfonamidophenylethyl)-4-(m-trifluoromethylphenyl)piperazine oxalate, as colorless crystals. mp 164° C. Anal. C,H,N. $^1$H NMR (DMSO-d$_6$): δ 2.85–3.15 (m, 8H), 3.0 (s, 3H), 3.35–3.50 (m, 4H), 7.0–7.5 (m, 8H), 9.73 (br s, 1H).

EXAMPLE 1a

Preparation of 1-(2-m-methanesulfonamidophenylethyl)-4-(m-trifluoromethylphenyl)piperazine hydrochloride 1-(2-m-Methanesulfonamidophenylethyl)-4-(m-trifluoromethylphenyl)piperazine (99%, 9.09 g, 21.3 mmol) was dissolved in minimal anhydrous diethyl ether and treated with one equivalent of HCl (1 M in Et$_2$O, 21.3 mL) and stirred. The resulting crude solid was taken to dryness under vacuum, then dissolved in minimal hot MeOH and allowed to slowly cool. The solution was further cooled to −10° C. before filtering. The filter cake was washed with ice-cold methanol and allowed to dry, yielding an off-white powder (5.50 g). The power was redissolved in minimal hot MeOH and allowed to cool to ambient temperature. The crystals were cooled to −10° C. and filtered. The filter cake was washed with cold MeOH and allowed to dry, yielding 1-(2-m-methanesulfonamidophenylethyl)-4-(m-trifluoromethylphenyl)piperazine hydrochloride (4.50 g, 45%): mp 198–199° C.; IR (KBr) 1606 cm$^{-1}$; $^1$H NMR (d$_6$-DMSO, 250 MHz, 6 mg/mL) δ 10.85 (bs, 1H), 9.78 (s, 1H), 7.47 (t, 1H), 7.31 (m, 3H), 7.06 (m, 4H), 3.98 (d, 2H), 3.63 (d, 2H), 3.15 (m, 8H), 2.99 (s, 3H); Anal. Calcd for C$_{20}$H$_{24}$F$_3$N$_3$O$_2$S.HCl: C, 51.78; H, 5.43; N, 9.06. Found: C, 51.69; H, 5.53; N, 8.94.

We claim:
1. A compound of the formula:

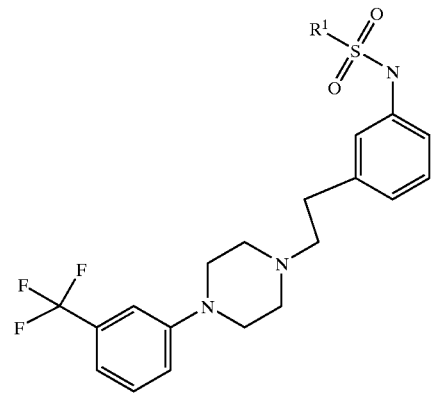

wherein R$^1$ represents C$_1$–C$_4$ alkyl;
or a pharmaceutically acceptable salts or solvate thereof.

2. The compound according to claim 1 wherein $R^1$ is methyl.

3. The compound according to claim 1 which is 1-(2-m-methanesulfonamidophenylethyl)-4-(m-trifluoromethylphenyl)piperazine hydrochloride.

4. A method of treating bladder over-activity or urinary incontinence in a patient in need of such treatment, comprising administering to the patient an effective amount of a compound of the formula:

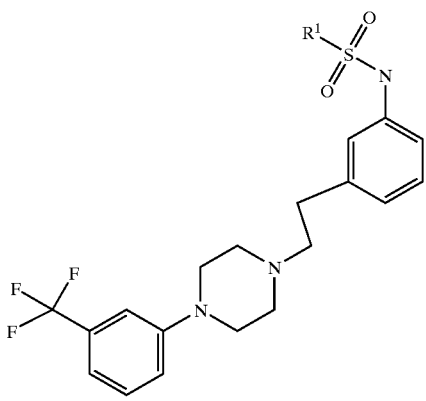

wherein $R^1$ represents $C_1$–$C_4$ alkyl;
or a pharmaceutically acceptable salts or solvate thereof.

5. The method of claim 4 wherein the urinary incontinence is urge urinary incontinence.

6. The method of claim 4 wherein the urinary incontinence is stress urinary incontinence.

7. The method of claim 4 wherein the urinary incontinence is mixed urinary incontinence.

8. A pharmaceutical composition comprising an effective amount of a compound of the formula:

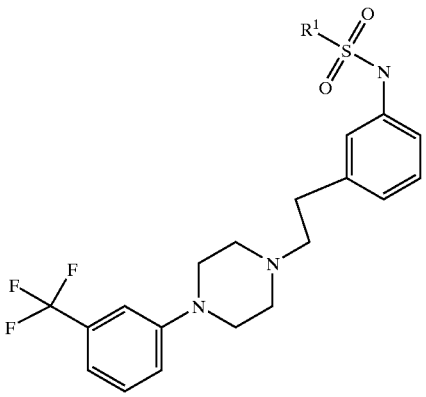

wherein $R^1$ represents $C_1$–$C_4$ alkyl;

or a pharmaceutically acceptable salt or solvate thereof, and one or more pharmaceutically acceptable diluents or carriers.

9. The pharmaceutical composition according to claim 8, wherein $R^1$ is methyl.

10. The pharmaceutical composition according to claim 8, which is 1-(2-m-methanesulfonamidophenylethyl)-4-(m-trifluoromethylphenyl)piperazine hydrochloride.

* * * * *